US010603298B2

(12) United States Patent
Chouchani et al.

(10) Patent No.: US 10,603,298 B2
(45) Date of Patent: Mar. 31, 2020

(54) SUCCINATE DEHYDROGENASE INHIBITORS (SDHI'S)

(71) Applicants: Medical Research Council, Wiltshire (GB); Cambridge Enterprise Limited, Cambridge (GB)

(72) Inventors: Edward Chouchani, Cambridge (GB); Thomas Krieg, Cambridge (GB); Michael Patrick Murphy, Cambridge (GB); Lorraine Work, Glasgow (GB); Christian Frezza, Cambridge (GB); Kourosh Saeb-Parsy, Cambridge (GB)

( * ) Notice: Subject to any disclaimer, the term of this patent is extended or adjusted under 35 U.S.C. 154(b) by 0 days.

(21) Appl. No.: 15/322,939

(22) PCT Filed: Jul. 3, 2015

(86) PCT No.: PCT/GB2015/051949
§ 371 (c)(1),
(2) Date: Dec. 29, 2016

(87) PCT Pub. No.: WO2016/001686
PCT Pub. Date: Jan. 7, 2016

(65) Prior Publication Data
US 2017/0135977 A1 May 18, 2017

(30) Foreign Application Priority Data
Jul. 3, 2014 (GB) .................................... 1411937.4

(51) Int. Cl.
*A61K 31/225* (2006.01)
(52) U.S. Cl.
CPC .................................. *A61K 31/225* (2013.01)
(58) Field of Classification Search
CPC .................................................. A61K 31/225
USPC ........................................................ 514/547
See application file for complete search history.

(56) References Cited

U.S. PATENT DOCUMENTS

| 2013/0116337 A1 | 5/2013 | Lopachin | |
| 2014/0128352 A1* | 5/2014 | Brand | G01N 33/5008 514/155 |

FOREIGN PATENT DOCUMENTS

| JP | 2001-521002 | 11/2001 |
| WO | 9921565 | 5/1999 |
| WO | 2005094236 | 10/2005 |
| WO | 200839085 | 4/2008 |
| WO | 2013152193 | 10/2013 |
| WO | 2014179187 | 11/2014 |

OTHER PUBLICATIONS

Drose, Molecular Pharmacology, vol. 79, No. 5, Jan. 28, 2011 pp. 814-822.*
Wojtovich, Basic Research in cardiology, 2009, 104(2), 121-129.*
Dzeja, American J of Physiology, vol. 284, No. 4, Part 02, Apr. 1, 2003.*
Ralph, Pharm. Research, vol. 28, No. 11, Aug. 24, 2011, 2695-2730.*
Tang, Evidence-Based Complementary and Alternative Medicine, vol. 104, No. 3, Jan. 1, 2013 (Jan. 1, 2013), pp. 330-11.*
Campos, Int. J. BioChem. And Cell Biology, vol. 44, No. 2, Nov. 1, 2011 (Nov. 1, 2011), pp. 262-265.*
Bouaziz, European journal of pharmacology, vol. 441, No. 1-2, Apr. 1, 2002 (Apr. 1, 2002), pp. 35-45.*
Dervartanian, Biochim. Biophys. Acta 92, 233-247 (1964).*
Tatjana, John, International Search Report and Written Opinion—International App No. PCT/GB15/51949 dated Sep. 28, 2015 Sep. 28, 2015.
Hu, Zhiwei, Chemical Preconditioning by 3-nitropropionic Acid Reduces Ischemia-reperfusion Injury in Rat Heart; Journal of Huazhung University of Science and Technology, 25(4); pp. 439-441 Jan. 1, 2005 Jan. 1, 2005.
Hirata, Toshiki, "Chemical Preconditioning" by 3-Nitropropionate Reduces Ischemia-Reperfusion Injury in Cardiac-Arrested Rat Lungs; Transplantation, vol. 71, No. 3, pp. 352-359 Feb. 15, 2001 Feb. 15, 2001.
Stottrup, Nicolaj, Inhibition of the malate-aspartate shuttle by pre-ischaemic aminooxyacetate loading of the heart induces cardioprotection; Cardiovascular Research vol. 88 pp. 257-266, 2010 Jan. 1, 2010 Jan. 1, 2010.
Wojtovich, Andrew, et al., The complex II inhibitor atpenin A5 protects against cardiac ischemia-reperfusion injury via activation of mitochondrial Katp channels; Basic Research Cardiology, 104; pp. 121-129, 2009 Feb. 26, 2009 Feb. 26, 2009.
Wojtovich, The endogenous mitochondrial complex II inhibitor malonate regulates mitochondrial ATP-sensitive potassium channels: Implications for ischemic preconditioning; Biochimica et Biophysica Acta, 1777, pp. 882-889, 2008 Apr. 8, 2008 Apr. 8, 2008.
Drose, A Common Mechanism Links Differently Acting Complex II Inhibitors to Cardioprotection: Modulation of Mitochondrial Reactive Oxygen Species Production; Molecular Pharmacology, vol. 79 No. 5, pp. 814-822 Jan. 28, 2011 Jan. 28, 2011.
Dzeja, Targeting nucleotide-requiring enzymes: implications for diazoxide-induced cardioprotection; American Journal of Physiology: Heart and Circulatory Physiology, American Physiological Society, vol. 284, No. 4 pp. H1048-H1056 Dec. 5, 2002 Dec. 5, 2002.
Ralph, Inhibitors of Succinate: Quinone Reductase/Complex II Regulate Production of Mitochondrial Reactive Oxygen Species and Protect Normal Cells from Ischemic Damage but induce Specific Cancer Cell Death Aug. 24, 2011 Aug. 24, 2011.
Tang, The Cardioprotective Effects of Citric Acid and L-Malic Acid on Myocardial Ischemia/Reperfusion Injury; Evidence-Based Complementary and Alternative Medicine, vol. 104, No. 3, pp. 1-12 Jan. 1, 2013 Jan. 1, 2013.

(Continued)

*Primary Examiner* — Nizal S Chandrakumar
(74) *Attorney, Agent, or Firm* — Thomas G. Peterson; Maynard Cooper & Gale

(57) ABSTRACT

The invention relates to a succinate dehydrogenase inhibitor or a prodrug and/or a pharmaceutically acceptable salt thereof for use in the treatment or prevention of reperfusion injury, such as ischemia-reperfusion injury, by inhibiting the accumulation of succinate, wherein the inhibitor or prodrug and/or pharmaceutically acceptable salt thereof is a cell-permeable reversible inhibitor of succinate dehydrogenase.

13 Claims, 24 Drawing Sheets

(56) References Cited

OTHER PUBLICATIONS

Campos, Oxaloacetate: A novel neuroprotective for acute ischemic stroke; The International Journal of Biochemistry and Cell Biology, vol. 44, No. 2, pp. 262-265 Nov. 1, 2011 Nov. 1, 2011.
Bouaziz, Mitochondrial respiratory chain as a new target for anti-ischemic molecules; European Journal of Pharmacology, vol. 441, No. 1-2, pp. 35-45 Apr. 1, 2002 Apr. 1, 2002.
Methner, Mitochondria selective S-nitrosation by mitochondria-targeted S-nitrosothiol protects against post-infarct heart failure in mouse hearts; European Journal of Heart Failure, vol. 16, No. 7, pp. 712-717 May 31, 2014 May 31, 2014.
Chouchani, Ischaemic accumulation of succinate controls reperfusion injury through mitochondrial ROS; Nature, vol. 515, No. 7527, pp. 431-435 Nov. 5, 2014 Nov. 5, 2014.
OECD SIDS Malonic Acid Diesters; Unep Publications, URL:http://www.inchem.org/documents/sids/sids/malonates.pdf Apr. 22, 2005 Apr. 22, 2005.
Ishii, Yumiko, "Office Action—Japan Application No. 2016-574359" Japan Patent Office; dated Feb. 18, 2019.

* cited by examiner

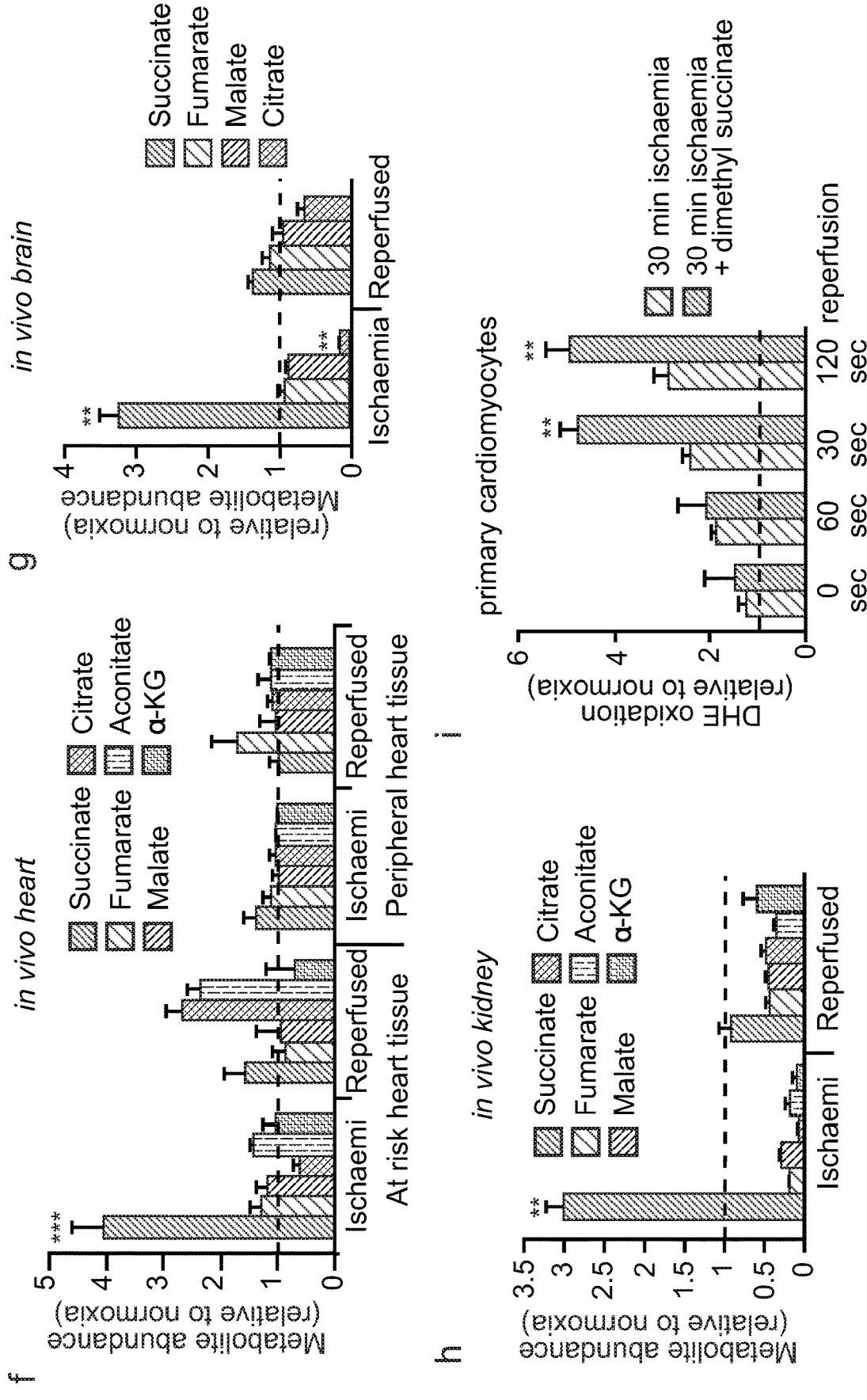

e a b a

Ischaemia b

Reperfusion

C  Normoxia

SUCCINATE DEHYDROGENASE INHIBITORS (SDHI'S)

CROSS-REFERENCE TO RELATED APPLICATIONS

This application is a national stage under 35 U.S.C. 371 of International Application PCT/GB2015/051949, filed on May 21, 2015 (currently published). International Application no. PCT/GB2015/051949 cites the priority of GB 1411937.4, filed 3 Jul. 2014.

FIELD OF THE INVENTION

The invention relates to a succinate dehydrogenase inhibitor or a prodrug and/or a pharmaceutically acceptable salt thereof for use in the treatment or prevention of reperfusion injury by inhibiting the accumulation of succinate, wherein the inhibitor or prodrug and/or pharmaceutically acceptable salt thereof is a cell-permeable and reversible inhibitor of succinate dehydrogenase.

BACKGROUND TO THE INVENTION

Succinate is known to build up in anaerobic conditions. For example, diving animals, hypoxic areas at the centre of tumours, and certain parasites can be observed to show elevated succinate in conditions of hypoxia. However, these studies are typically in the context of attempting to kill cells or to block or remove the cells from the system under study. Moreover, these systems are not always comparable the conditions experienced by mammalian cells under hypoxia. For example, in bacteria the two enzymatic activities involved in succinate metabolism are present in two separate enzymes [rather than in the same single enzyme succinate dehydrogenase (SDH) in mammalian cells].

Succinate has been studied in certain in vitro systems. It is possible that reactive oxygen species (ROS) generation via succinate has been observed in certain in vitro systems. However, such observations have been largely regarded as in vitro curiosities rather than a genuine reflection of possible conditions in vivo.

Succinate has been studied for oxygen sensing applications. There have been attempts to block the succinate in order to try to achieve an anti-inflammatory effect in the prior art.

There is no known experimental connection in the prior art linking succinate accumulation in vivo to ROS production by mitochondrial complex I due to succinate oxidation upon reperfusion.

Hu et al, *Journal of Huazhong University of Science and Technology, Medical Sciences*, vol. 25, 2005, pages 439-441 and Hirata et al, *Transplantation*, vol. 71, 2001, pages 352-359 have both shown that chemical preconditioning using 3-nitropropionate reduced ischemia-reperfusion injury in rats. The compound 3-nitropropionate is an inhibitor of mitochondrial complex II. Wojtovich et al, *Basic Research in Cardiology*, vol. 104, 2009, pages 121-129 have reported that the complex II inhibitor atpennin A5 protects the heart against simulated ischemia-reperfusion injury through a $mK_{ATP}$ channel dependent mechanism. However, inhibitors such as 3-nitropropionate and atpennin A5 have the disadvantage that they are irreversible. As a consequence, any complex II that binds to such irreversible inhibitors is permanently prevented from carrying out its normal function.

Drose et al, *Molecular Pharmacology*, vol. 79, 2011, pages 814-822 studied several cardioprotective complex II inhibitors including 2-thenoyltrifluoroacetone (TTFA), 3-nitropropionate, atpennin A5 and malonate. Of the inhibitors tested, malonate required the highest concentration, in millimolar levels, to achieve half-maximal inhibition compared to nanomolar levels required for atepennin A5. In addition, malonate has the disadvantage that it is not cell-permeable. The other inhibitors TTFA, 3-nitropropionate and atpennin A5 have the disadvantage that they are irreversible.

Dimethylmalonate is a known compound. Malonate and its derivatives are industrial compounds used as feed stocks for polymer formation. There is no known teaching in the prior art for use of malonate derivative, such as dimethylmalonate, as a prodrug of an inhibitor of SDH. The prodrug dimethyl malonate will be hydrolysed in vivo to malonate which is an inhibitor of SDH.

The present invention seeks to overcome problem(s) associated with the prior art.

SUMMARY OF THE INVENTION

The inventors performed an extensive metabolomic survey to identify metabolites which are accumulated during ischaemia. As part of a carefully controlled study, this metabolomics analysis was conducted in parallel in a wide range of tissue types. A number of metabolites were observed to vary in ischaemic conditions in different tissues. However, despite this finding the inventors persisted with their analysis and selected only those metabolites which were similarly affected across the full spectrum of tissues studied. In this way, the inventors were ingeniously able to select metabolites which were more likely to be common to the effect of ischaemia.

In addition, the inventors went on to analyse the effect of reperfusion on the analytes. This allowed the inventors to select only three metabolites (hypoxanthine, xanthine and succinate) which behaved similarly across a range of tissue types in accumulation during ischaemia. Most surprisingly, the inventors observed that of these three, only succinate could plausibly play a role in the generation of reactive oxygen species following reperfusion. It was these dramatic insights which singled out succinate as accumulating during ischaemia, and as being rapidly metabolised and involved in the production of reactive oxygen species following reperfusion, upon which the invention is based.

It was a surprise to the inventors that the succinate disappeared so fast upon reperfusion. It was also a surprise to discover that succinate was the source of reactive oxygen species following restoration of metabolic function under normoxic conditions. It was a further surprise that multiple organs share the same metabolic signature, demonstrating that the succinate metabolism is a widely applicable phenomenon within mammalian cells' response to ischaemic conditions.

Thus in one aspect the invention provides a succinate dehydrogenase inhibitor or a prodrug and/or a pharmaceutically acceptable salt thereof for use in the treatment or prevention of reperfusion injury by inhibiting the accumulation of succinate, wherein the inhibitor or prodrug and/or pharmaceutically acceptable salt thereof is a cell-permeable and reversible inhibitor of succinate dehydrogenase.

In a further aspect, the invention provides a method of treating or preventing a reperfusion injury in a subject, the method comprising administering to the subject an effective amount of a succinate dehydrogenase inhibitor a prodrug and/or a pharmaceutically acceptable salt thereof that is a cell-permeable and reversible inhibitor of succinate dehydrogenase.

In a further aspect, the invention provides a succinate dehydrogenase inhibitor or a prodrug and/or a pharmaceutically acceptable salt thereof for use in the treatment or prevention of reperfusion injury, wherein the inhibitor or prodrug and/or pharmaceutically acceptable salt thereof is a cell-permeable and reversible inhibitor of succinate dehydrogenase.

In a further aspect, the invention provides a succinate dehydrogenase inhibitor or a prodrug and/or a pharmaceutically acceptable salt thereof for use in the treatment or prevention of reperfusion injury by inhibiting the accumulation of succinate, wherein the inhibitor or prodrug and/or pharmaceutically acceptable salt thereof is a cell-permeable and reversible inhibitor of succinate dehydrogenase.

Definitions $C_{1-12}$ alkyl: refers to straight chain and branched saturated hydrocarbon groups, generally having from 1 to 12 carbon atoms. Examples of alkyl groups include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, n-octyl, n-nonane, n-decane, n-undecane, n-dodecane and the like.

"Drug", "drug substance", "active pharmaceutical ingredient", and the like, refer to a compound (e.g., compounds of Formula (I) and compounds specifically named below) that may be used for treating a subject in need of treatment.

"Excipient" refers to any substance that may influence the bioavailability of a drug, but is otherwise pharmacologically inactive.

"Pharmaceutically acceptable" substances refers to those substances which are within the scope of sound medical judgment suitable for use in contact with the tissues of subjects without undue toxicity, irritation, allergic response, and the like, commensurate with a reasonable benefit-to-risk ratio, and effective for their intended use.

"Pharmaceutical composition" refers to the combination of one or more drug substances and one or more excipients.

The term "subject" as used herein refers to a human or non-human mammal. Examples of non-human mammals include livestock animals such as sheep, horses, cows, pigs, goats, rabbits and deer; and companion animals such as cats, dogs, rodents, and horses.

"Therapeutically effective amount" of a drug refers to the quantity of the drug or composition that is effective in treating a subject and thus producing the desired therapeutic, ameliorative, inhibitory or preventative effect. The therapeutically effective amount may depend on the weight and age of the subject and the route of administration, among other things.

"Treating" refers to reversing, alleviating, inhibiting the progress of, or preventing a disorder, disease or condition to which such term applies, or to reversing, alleviating, inhibiting the progress of, or preventing one or more symptoms of such disorder, disease or condition.

"Treatment" refers to the act of "treating", as defined immediately above.

"Preventing" refers to a reduction of the risk of acquiring a given disease or disorder, that is, causing the clinical symptoms not to develop. Hence, "preventing" refers to the prophylactic treatment of a subject in need thereof. The prophylactic treatment can be accomplished by administering an appropriate dose of a therapeutic agent to a subject having a predisposition to a disorder, or at risk of developing a disorder, even though symptoms of the disorder are absent or minimal, thereby substantially averting onset of the disorder.

The term "prodrug" means a compound which is, after administration to a subject, subjected to a structural change such as hydrolysis in vivo, preferably in blood, to produce an SDHi or a salt thereof. For example, various means for producing prodrugs from pharmaceutical compounds having carboxylic acid, amino group, hydroxyl group or the like are known, and one of ordinary skill in the art can choose appropriate means. Types of the prodrug of an SDHi or a salt thereof are not particularly limited. For example, where an SDHi has one or more carboxylic acids, an example includes a prodrug wherein one or more of the carboxylic acids are converted into an ester. Preferred examples include ester compounds such as methyl ester or diemethyl esters.

"Succinate dehydrogenase inhibitor" or "SDHi" refers to compound that inhibit the action of succinate dehydrogenase.

As used herein the term "comprising" means "consisting at least in part of". When interpreting each statement in this specification that includes the term "comprising", features other than that or those prefaced by the term may also be present. Related terms such as "comprise" and "comprises" are to be interpreted in the same manner.

Succinate Dehydrogenase Inhibitors (SDHi's) or Prodrugs Thereof

The SDHi or a prodrug and/or a pharmaceutically acceptable salt thereof is useful in the treatment or prevention of reperfusion injury by inhibiting the accumulation of succinate. Thus, administration of the SDHi or a prodrug and/or a pharmaceutically acceptable salt thereof treats or prevents reperfusion injury in a tissue of a subject, such as an ischaemic myocardium, by decreasing the amount of succinate observed at reperfusion in the tissue compared to the amount of succinate observed at reperfusion without administration of the SDHi or a prodrug and/or a pharmaceutically acceptable salt thereof.

The SDHi is a reversible inhibitor of SDH. The reversibility of the SDHi is important as this enables the inhibitor, over time, to be removed from the mitochondrial complex by competitive binding so that its effect will be transient. As a result, the complex may return to performing its normal functions.

For an SDHi that acts through the succinate site, the reversibility of the SDHi may be determined by measuring and comparing the infarct size of (1) a heart treated with the SDHi; (2) an untreated heart; and (3) a heart treated with the SDHi+dimethyl succinate. Cardioprotection is shown if the infarct size is reduced in the heart treated with the SDHi in comparison to that of an untreated heart. The reversibility of the SDHi is demonstrated if the cardioprotection shown by the heart treated with the SDHi is suppressed by adding back dimethyl succinate. This procedure is discussed in the Examples using triphenyltetrazolium chloride staining to determine the infarct size of the heart (see also FIGS. 4b & c).

The efficacy of an SDHi may be assessed by determining the ability of the SDHi to prevent succinate accumulation during ischaemia. The ability of the SDHi to prevent succinate accumulation during ischaemia may be determined by measuring succinate levels in tissues by liquid chromatography/mass spectrometry (LC/MS) as detailed in the metabolomic analysis in the Examples. The reversibility of the SDHi may be shown by comparing the succinate levels following treatment with the SDHi with the succinate levels following treatment with the SDHi plus dimethyl succinate.

The SDHi or a prodrug and/or a pharmaceutically acceptable salt thereof is membrane permeable. This membrane permeability enables the compound to enter the cell and accumulate.

Membrane permeability may be assayed in cell experiments by measuring oxygen consumption rate (OCR) and by driving this with dimethyl succinate and then inhibiting this by adding an SDHi or a prodrug and/or pharmaceutically acceptable salt thereof (such as dimethyl malonate) so the efficacy and timescale of uptake and hydrolysis of the SDHi or a prodrug and/or pharmaceutically acceptable salt thereof can be assessed. In addition, as shown in FIG. 5a the cell permeability of the compound may be determined by comparing the level of the compound in an untreated cell with that of a treated cell. Typically, the level of the compound may be determined using LC/MS as detailed in the metabolomic analysis in the Examples.

More suitably, the SDHi or a prodrug and/or a pharmaceutically acceptable salt thereof is a prodrug of an SDHi or a pharmaceutically acceptable salt thereof.

Most suitably, the SDHi or a prodrug and/or a pharmaceutically acceptable salt thereof is a prodrug.

Suitably the SDHi binds to SDH.

Suitably the SDHi or a prodrug and/or pharmaceutically acceptable salt thereof has the general formula (I):

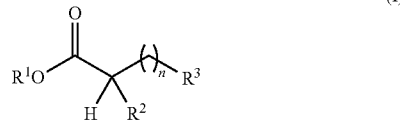

(I)

wherein:
n is 0 or 1;
$R^1$ is selected from $C_{1-12}$ alkyl;
$R^2$ is selected from H and OH;
$R^3$ is selected from $CO_2R^4$, and $C(O)$—$CO_2R^4$; and
$R^4$ is selected from $C_{1-12}$ alkyl.

Suitably the succinate dehydrogenase inhibitor or a prodrug and/or pharmaceutically acceptable salt thereof is selected from $R^1O_2C$—$CH_2$—$CO_2R^4$, $R^1O_2C$—$CH(OH)$—$CH_2$—$CO_2R^4$, $R^1O_2C$—$CH_2$—$C(O)$—$CO_2R^4$.

More suitably the succinate dehydrogenase inhibitor or a prodrug and/or pharmaceutically acceptable salt thereof is selected from $R^1O_2C$—$CH_2$—$CO_2R^4$, wherein $R^1$ and $R^4$ are independently selected from methyl, ethyl, n-propyl, iso-propyl, n-butyl, s-butyl, t-butyl.

Most suitably the SDHi or a prodrug and/or pharmaceutically acceptable salt thereof is a malonate compound.

Suitably the SDHi or a prodrug and/or pharmaceutically acceptable salt thereof may comprise a cell permeable malonate.

Suitably the malonate SDHi or a prodrug and/or pharmaceutically acceptable salt thereof of the invention is an ethyl ester malonate.

Most suitably the succinate dehydrogenase inhibitor or a prodrug and/or pharmaceutically acceptable salt thereof is dimethyl malonate.

Dimethylmalonate is advantageous as it has extremely low toxicity. For example, the $LD_{50}$ of dimethylmalonate is approximately 5 gms per kilogram when administered orally.

Suitably binding of the SDHi to SDH is at the succinate binding site. Suitably this is competitive binding with succinate.

Suitably the SDHi that binds SDH at the succinate binding site or a prodrug and/or pharmaceutically acceptable salt thereof is selected $R^1O_2C$—$CH_2$—$CO_2R^4$, $R^1O_2C$—$CH(OH)$—$CH_2$—$CO_2R^4$ and $R^1O_2C$—$CH_2$—$C(O)$—$CO_2R^4$.

Suitably the SDHi binds SDH at the ubiquinone binding site. Suitably this binding is competitive binding with quinone.

Most suitably SDH is useful in the invention inhibit re-oxidation of succinate under normoxic conditions.

Suitably the SDHi of the invention is a "complex II" inhibitor.

The SDHi of the invention is a reversible inhibitor.

Suitably the SDHi of the invention is a reversible SDHi.

$R^1$

Suitably $R^1$ is selected from methyl, ethyl, propyl, butyl, pentyl and hexyl.

More suitably $R^1$ is selected from methyl and ethyl.

$R^2$

Suitably $R^2$ is H.

$R^3$

Suitably $R^3$ is $CO_2R^4$.

$R^4$

Suitably $R^4$ is selected from methyl, ethyl, propyl, butyl, pentyl and hexyl.

More suitably $R^4$ is selected from methyl and ethyl.

Administration and Timing

Suitably the SDHi or a prodrug and/or pharmaceutically acceptable salt thereof is administered orally, topically, subcutaneous, parenterally, intramuscular, intra-arterial and/or intravenously.

More suitably the SDHi or a prodrug and/or pharmaceutically acceptable salt thereof is administered intravenously.

The SDHi or a prodrug and/or pharmaceutically acceptable salt thereof may be administered by direct injection into the coronary artery.

Suitably the SDHi or a prodrug and/or pharmaceutically acceptable salt thereof of the invention is administered before ischaemia. In such circumstances the SDHi or a prodrug and/or pharmaceutically acceptable salt thereof is administered to a subject at risk of ischaemia.

Suitably the SDHi or a prodrug and/or pharmaceutically acceptable salt thereof of the invention is administered following ischaemia.

Suitably the SDHi or a prodrug and/or pharmaceutically acceptable salt thereof of the invention is administered before reperfusion.

Suitably the SDHi or a prodrug and/or pharmaceutically acceptable salt thereof of the invention is administered as soon as possible after the initiation of reperfusion.

Suitably the SDHi or a prodrug and/or pharmaceutically acceptable salt thereof of the invention is administered within five minutes of reperfusion commencing. Suitably the SDHi or a prodrug and/or pharmaceutically acceptable salt thereof of the invention is administered within four minutes of reperfusion commencing; within three minutes of reperfusion commencing; within two minutes of reperfusion commencing; or within one minute of reperfusion commencing.

Suitably the SDHi or a prodrug and/or pharmaceutically acceptable salt thereof of the invention is administered before surgery.

Suitably the SDHi or a prodrug and/or pharmaceutically acceptable salt thereof of the invention is administered during surgery.

Suitably the SDHi or a prodrug and/or pharmaceutically acceptable salt thereof of the invention is administered to organs intended to be preserved before ischaemia.

Suitably the SDHi or a prodrug and/or pharmaceutically acceptable salt thereof of the invention is administered to organs to be preserved as soon as possible after ischaemia.

Suitably the SDHi or a prodrug and/or pharmaceutically acceptable salt thereof of the invention is administered to organs to be preserved as soon as possible after reperfusion.

Suitably the SDHi or a prodrug and/or pharmaceutically acceptable salt thereof of the invention is administered to organs to be preserved within five minutes of reperfusion.

Suitably the SDHi or a prodrug and/or pharmaceutically acceptable salt thereof of the invention is administered within four minutes of reperfusion commencing; within three minutes of reperfusion commencing; within two minutes of reperfusion commencing; or within one minute of reperfusion commencing.

Suitably the SDHi or a prodrug and/or pharmaceutically acceptable salt thereof of the invention finds application in organ transplantation.

It is an advantage of the invention that a protective treatment is provided. There are no licensed protective compounds on the market at present.

Suitably the SDHi or a prodrug and/or pharmaceutically acceptable salt thereof of the invention is quickly metabolised in mammals.

It is an advantage of malonate SDHi's or a prodrug and/or pharmaceutically acceptable salt thereof that they are metabolised in mammalian cells. Cell permeable malonate derivatives are suitably metabolised in order to release malonate once inside the cell. Malonate itself is advantageously metabolised by natural metabolic pathways within the cell. More specifically, malonate is metabolised into part of the fat decomposition pathway naturally present in mammalian cells. This offers the advantage that there are no side effects or by products of metabolites of the SDHi or a prodrug and/or pharmaceutically acceptable salt thereof of the invention when the SDHi or a prodrug and/or pharmaceutically acceptable salt thereof is a malonate compound.

Suitably the succinate dehydrogenase inhibitor or a prodrug and/or pharmaceutically acceptable salt thereof may be administered at a dose of 0.1-50 mg/kg of subject/min for 1 to 30 minutes. More suitably, the succinate dehydrogenase inhibitor or a prodrug and/or pharmaceutically acceptable salt thereof may be administered at a dose of 0.5-20 mg/kg of subject/min for 1 to 30 minutes. More suitably, the succinate dehydrogenase inhibitor or a prodrug and/or pharmaceutically acceptable salt thereof may be administered at a dose of 1-10 mg/kg of subject/min for 1 to 30 minutes.

DETAILED DESCRIPTION OF THE INVENTION

From the candidate metabolites analysed, the inventors excluded those which varied differently in different tissues. For example, some metabolites were elevated in one tissue yet decreased in another following ischaemic conditions. Some metabolites were affected to different levels. Other metabolites did not appear to be affected at all. Further metabolites did not appear affected in all of the tissue types studied. The inventors systematically examined the data and removed each of the metabolites possessing these diverse criteria so as to select only those metabolites exhibiting common properties across ischaemia of a range of different tissues studied.

A key finding upon which the invention is based is the rapid return of succinate to normal levels following reperfusion. This is illustrated for example in FIG. 1E where it can be seen that succinate levels descend sharply to normal within only five minutes of reperfusion. The rapidity of this response is remarkable. This contributes to the evidence accumulated by the inventors that succinate is forming the reservoir of electrons which is created during ischaemic conditions. Moreover, the timing is extraordinary since it overlaps precisely with the time course of damage inflicted on tissue from a reperfusion. It is this same five minute window observed by the inventors during which most damage is caused, which also follows exactly the time course of succinate metabolism following reperfusion.

Applications

Suitably, the invention relates to a succinate dehydrogenase inhibitor or a prodrug and/or a pharmaceutically acceptable salt thereof for use in the treatment or prevention of reperfusion injury by inhibiting the accumulation of succinate.

Suitably, the invention relates to a succinate dehydrogenase inhibitor or a prodrug and/or a pharmaceutically acceptable salt thereof for use in the treatment or prevention of reperfusion injury by inhibiting succinate transport.

Suitably, the invention relates to a succinate dehydrogenase inhibitor or a prodrug and/or a pharmaceutically acceptable salt thereof for use in the treatment or prevention of reperfusion injury by inhibiting succinate oxidation.

The invention finds application in surgery.

The invention finds application in organ preservation.

The invention finds application in the reduction or inhibition of ROS production.

The invention finds application in the inhibition or prevention of succinate accumulation.

The invention finds application in slowing the release of ROS following reperfusion.

The invention finds application in all forms of the elective surgery. In these applications of the invention, the treatment may be preventative, i.e. preventative against production of ROS following reperfusion.

Reperfusion Injury

Suitably, the reperfusion injury is an ischaemia-reperfusion injury.

Suitably, the reperfusion injury is a result of a disorder selected from an abdominal aortic aneurysm, atherosclerosis, artery disease, burns, cancer, cardiac arrest, cerebrovascular disease, cerebral edema secondary to stroke, cerebral damage, chronic obstructive pulmonary disease, congestive heart disease, constriction after percutaneous transluminal coronary angioplasty, coronary disease, diabetes, hypertension, hypoxia during/after childbirth, mechanical trauma resulting from crush injury or surgery, migraine, myocardial infarction, (non-fatal) drowning, peripheral vascular disease, pulmonary vascular disease, regenerative medicine, reperfusion after cardiac surgery, reperfusion after stroke, retinal vascular disease, stroke and surgical tissue reperfusion injury.

Suitably the surgical tissue reperfusion injury may be the result of liver, kidney or bowel surgery.

Surgical tissue reperfusion injury may be the result of elective surgical operations where an organ is exposed to a period of ischaemia include liver surgery (when the blood supply to the liver is temporarily clamped to enable dissection/partial resection) and kidney surgery (e.g., partial resection of a tumour).

A common cause of cerebral damage is systemic hypotension during surgery, resulting in temporary hypoperfusion of the brain.

More suitably, the reperfusion injury is a result of a disorder selected from an abdominal aortic aneurysm, atherosclerosis, artery disease, cardiac arrest, cerebrovascular disease, cerebral edema secondary to stroke, congestive heart disease, constriction after percutaneous transluminal coronary angioplasty, coronary disease, mechanical trauma resulting from crush injury or surgery, myocardial infarction, peripheral vascular disease, pulmonary vascular disease, reperfusion after cardiac surgery, reperfusion after stroke, retinal vascular disease, stroke and surgical tissue reperfusion injury.

Suitably the surgery is vascular surgery, heart bypass surgery or transplant surgery.

More suitably, the reperfusion injury is a result of a disorder selected from reperfusion after stroke, stroke and myocardial infarction.

Suitably the reperfusion injury is a reperfusion injury in an organ to be preserved. Suitably organs to be preserved may be selected from heart, intestine, kidney, liver, lung, pancreas and skin.

Organs may be preserved for the purpose of transplantation, or as a source of cells and tissues for use in regenerative medicine (for example, isolation of stem cells).

More suitably, the reperfusion injury is a reperfusion injury in regenerative medicine. The future of regenerative medicine is based on the principle of (cryo-) preserving stem cells and stem cell-derived cells and tissues under likely anoxic condition, with subsequent adoptive transfer and/or transplantation into an oxygenated recipient.

Combinations

The SDHi or a prodrug and/or pharmaceutically acceptable salt thereof of the invention may be administered in combination with a treatment used or intended to remove a blockage in blood flow.

The SDHi or a prodrug and/or pharmaceutically acceptable salt thereof of the invention may be administered in combination with one or more of stents, MitoSNO, blood thinning agents, lysis agents, blood preservation solutions, organ preservation solutions or any other treatment used or intended to remove a blockage in blood flow.

Suitably blood or organ preservation solutions may include crystalloid and non-crystalloid solutions including but not limited to saline, human albumin solution, Hartmann's solution and gelofusin.

MitoSNO may be prepared as described in WO2008039085.

Suitably the blood thinning agents may be selected from Coumadin™ (warfarin); Pradaxa™ (dabigatran); Xarelto™ (rivaroxaban) and Eliquis™ (apixaban), Fondaparinux, unfractionated heparin, low molecular weight heparins including but not limited to enoxaparin and deltaparin, thrombolytic agents including but not limited to Streptokinase (SK), Urokinase, Lanoteplase, Reteplase, Staphylokinase and Tenecteplase.

The SDHi or a prodrug and/or pharmaceutically acceptable salt thereof of the invention may be administered as a pharmaceutical composition comprising an SDHi and a pharmaceutically acceptable excipient, carrier or diluent.

Suitable excipients, carriers and diluents can be found in standard pharmaceutical texts. See, for example, *Handbook for Pharmaceutical Additives*, 3rd Edition (eds. M. Ash and I. Ash), 2007 (Synapse Information Resources, Inc., Endicott, N.Y., USA) and *Remington: The Science and Practice of Pharmacy*, 21st Edition (ed. D. B. Troy) 2006 (Lippincott, Williams and Wilkins, Philadelphia, USA) which are incorporated herein by reference.

Excipients for use in the compositions of the invention include, but are not limited to microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavouring agents, colouring matter or dyes, and, if so desired, emulsifying and/or suspending agents as well, together with such diluents as water, ethanol, propylene glycol, glycerin and various like combinations thereof.

Pharmaceutical carriers include solid diluents or fillers, sterile aqueous media and various non-toxic organic solvents, and the like.

Pharmaceutically acceptable carriers include gums, starches, sugars, cellulosic materials, and mixtures thereof. The compound can be administered to a subject by, for example, subcutaneous implantation of a pellet. The preparation can also be administered by intravenous, intra-arterial, or intramuscular injection of a liquid preparation oral administration of a liquid or solid preparation, or by topical application. Administration can also be accomplished by use of a rectal suppository or a urethral suppository.

Further, as used herein "pharmaceutically acceptable carriers" are well known to those skilled in the art and include, but are not limited to, 0.01-0.1M and preferably 0.05M phosphate buffer or 0.9% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Pharmaceutically acceptable parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Pharmaceutically acceptable carriers for controlled or sustained release compositions administerable according to the invention include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Pharmaceutically acceptable carriers include compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski and Davis, *Soluble Polymer-Enzyme Adducts. Enzymes as Drugs*, Hocenberg and Roberts, eds., Wiley-Interscience, New York, N.Y., (1981), pp 367-383; and [65]). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

Further particular and preferred aspects are set out in the accompanying independent and dependent claims. Features of the dependent claims may be combined with features of the independent claims as appropriate, and in combinations other than those explicitly set out in the claims.

Isomers, Salts and Solvates

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; alpha- and beta-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OOH.

A reference to a class of structures may well include structurally isomeric forms falling within that class (e.g. C$_{1-67}$ alkyl includes n-propyl and iso-propyl; butyl includes n-, iso-, sec-, and tert-butyl; methoxyphenyl includes ortho-, meta-, and para-methoxyphenyl).

The above exclusion does not apply to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hyroxyazo, and nitro/aci-nitro.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof.

Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Unless otherwise specified, a reference to a particular compound also includes ionic, tautomeric, salt, solvate, protected forms, and combinations thereof, for example, as discussed below.

An example of a combination thereof is where a reference to an SDHi includes a salt of a tautomer. For example, a reference to the compound diethyl malate includes the sodium salt of the enolate form as shown below:

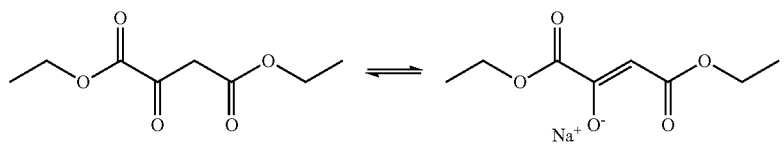

SDHi's, which include compounds specifically named above, may form pharmaceutically acceptable complexes, salts, solvates and hydrates. These salts include nontoxic acid addition salts (including di-acids) and base salts.

If the compound is cationic, or has a functional group which may be cationic (e.g. —NH$_2$ may be —NH$_3$), then an acid addition salt may be formed with a suitable anion. Examples of suitable inorganic anions include, but are not limited to, those derived from the following inorganic acids hydrochloric acid, nitric acid, nitrous acid, phosphoric acid, sulfuric acid, sulphurous acid, hydrobromic acid, hydroiodic acid, hydrofluoric acid, phosphoric acid and phosphorous acids. Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose. Such salts include acetate, adipate, aspartate, benzoate, besylate, bicarbonate, carbonate, bisulfate, sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfonate, naphthylate, 2-napsylate, nicotinate, nitrate, orotate, oxalate, palmitate, pamoate, phosphate, hydrogen phosphate, dihydrogen phosphate, pyroglutamate, saccharate, stearate, succinate, tannate, tartrate, tosylate, trifluoroacetate and xinofoate salts.

For example, if the compound is anionic, or has a functional group which may be anionic (e.g. —COOH may be —COO—), then a base salt may be formed with a suitable cation. Examples of suitable inorganic cations include, but are not limited to, metal cations, such as an alkali or alkaline earth metal cation, ammonium and substituted ammonium cations, as well as amines. Examples of suitable metal cations include sodium ($Na^+$) potassium ($K^+$), magnesium ($Mg^{2+}$), calcium ($Ca^{2+}$), zinc ($Zn^{2+}$), and aluminum ($Al^{3+}$). Examples of suitable organic cations include, but are not limited to, ammonium ion (i.e. $NH^{4+}$) and substituted ammonium ions (e.g. $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$. Examples of suitable amines include arginine, N,N'-dibenzylethylenediamine, chloroprocaine, choline, diethylamine, diethanolamine, dicyclohexylamine, ethylenediamine, glycine, lysine, N-methylglucamine, olamine, 2-amino-2-hydroxymethyl-propane-1,3-diol, and procaine. For a discussion of useful acid addition and base salts, see S. M. Berge et al., *J. Pharm. Sci.* (1977) 66:1-19; see also Stahl and Wermuth, *Handbook of Pharmaceutical Salts: Properties, Selection, and Use* (2011)

Pharmaceutically acceptable salts may be prepared using various methods. For example, one may react SDHi with an appropriate acid or base to give the desired salt. One may also react a precursor of the compound of SDHi with an acid or base to remove an acid- or base-labile protecting group or to open a lactone or lactam group of the precursor. Additionally, one may convert a salt of the compound of SDHi to another salt through treatment with an appropriate acid or base or through contact with an ion exchange resin. Following reaction, one may then isolate the salt by filtration if it precipitates from solution, or by evaporation to recover the salt. The degree of ionization of the salt may vary from completely ionized to almost non-ionized.

It may be convenient or desirable to prepare, purify, and/or handle a corresponding solvate of the active compound. The term "solvate" describes a molecular complex comprising the compound and one or more pharmaceutically acceptable solvent molecules (e.g., EtOH). The term "hydrate" is a solvate in which the solvent is water. Pharmaceutically acceptable solvates include those in which the solvent may be isotopically substituted (e.g., $D_2O$, acetone-d6, DMSO-d6).

A currently accepted classification system for solvates and hydrates of organic compounds is one that distinguishes between isolated site, channel, and metal-ion coordinated solvates and hydrates. See, e.g., K. R. Morris (H. G. Brittain ed.) Polymorphism in Pharmaceutical Solids (1995). Isolated site solvates and hydrates are ones in which the solvent (e.g., water) molecules are isolated from direct contact with each other by intervening molecules of the organic compound. In channel solvates, the solvent molecules lie in lattice channels where they are next to other solvent molecules. In metal-ion coordinated solvates, the solvent molecules are bonded to the metal ion.

When the solvent or water is tightly bound, the complex will have a well-defined stoichiometry independent of humidity. When, however, the solvent or water is weakly bound, as in channel solvates and in hygroscopic compounds, the water or solvent content will depend on humidity and drying conditions. In such cases, non-stoichiometry will typically be observed.

Further particular and preferred aspects are set out in the accompanying independent and dependent claims. Features of the dependent claims may be combined with features of the independent claims as appropriate, and in combinations other than those explicitly set out in the claims.

A wide variety of compounds of SDHi's are commercially available. Derivatives of such commercially available compounds may be prepared by carrying out functional group interconversions or making substitutions and carrying out common reactions as are known in the art. Common techniques and reactions, including oxidations, reductions, and so on, separation techniques (extraction, evaporation, precipitation, chromatography, filtration, trituration, crystallization, and the like), and analytical procedures, are known to persons of ordinary skill in the art of organic chemistry. The details of such reactions and techniques can be found in a number of treatises, including Richard Larock, *Comprehensive Organic Transformations, A Guide to Functional Group Preparations,* 2nd Ed (2010), and the multi-volume series edited by Michael B. Smith and others, *Compendium of Organic Synthetic Methods* (1974 et seq.). Starting materials and reagents may be obtained from commercial sources or may be prepared using literature methods. In addition, in some instances, reaction intermediates may be used in subsequent steps without isolation or purification (i.e., in situ).

Certain compounds can be prepared using protecting groups, which prevent undesirable chemical reaction at otherwise reactive sites. Protecting groups may also be used to enhance solubility or otherwise modify physical properties of a compound. For a discussion of protecting group strategies, a description of materials and methods for installing and removing protecting groups, and a compilation of useful protecting groups for common functional groups, including amines, carboxylic acids, alcohols, ketones, aldehydes, and so on, see T. W. Greene and P. G. Wuts, *Protecting Groups in Organic Chemistry,* 4th Edition, (2006) and P. Kocienski, *Protective Groups,* 3rd Edition (2005).

Generally, chemical transformations may be carried out using substantially stoichiometric amounts of reactants, though certain reactions may benefit from using an excess of one or more of the reactants. Additionally, many of the suitable reactions may be carried out at about room temperature (RT) and ambient pressure, but depending on reaction kinetics, yields, and so on, some reactions may be run at elevated pressures or employ higher temperatures (e.g., reflux conditions) or lower temperatures (e.g., −78° C. to 0° C.). Any reference in the disclosure to a stoichiometric range, a temperature range, a pH range, etc., whether or not expressly using the word "range," also includes the indicated endpoints.

BRIEF DESCRIPTION OF THE DRAWINGS

Embodiments of the present invention will now be described further, with reference to the accompanying drawings, in which:

FIG. 1: (b) HIVE plot comparative analysis of metabolites significantly accumulated across all ischaemic tissues in vivo. Metabolites accumulated commonly across all tissues are highlighted.

FIG. 1: (c) Prevalence of accumulation of metabolites in murine tissues during ischaemia.

FIG. 1: (d) Profile of mitochondrial citric acid cycle (CAC) metabolite levels following ischaemia across five ischaemic tissue conditions. n=3-4 mice per tissue, per group.

FIG. 1: (e) Time course of CAC metabolite levels during myocardial ischaemia and reperfusion for 5 min in the ex vivo heart. n=4 mouse hearts per group.

FIG. 1: (f) CAC metabolite levels during in vivo myocardial IR in at risk and peripheral heart tissue following ischaemia and after 5 min reperfusion. n=3-5 mice per group.

FIG. 1: (g) CAC metabolite levels during in vivo brain IR immediately following ischaemia and following 5 min reperfusion. n=3 rats per group.

FIG. 1: (h) CAC metabolite levels during in vivo kidney IR immediately following ischaemia and after 5 min reperfusion. n=3 mice per group.

FIG. 1: (i) Effect of succinate on ROS production assessed by dihydroethidium (DHE) oxidation in adult primary cardiomyocytes during IR. n=3 independent cardiomyocyte preparations per group.* $p<0.05$,  $p<0.01$, * $p<0.001$. Data are shown as the mean±s.e.m of at least three replicates.

FIG. 2: (b) $^{13}C$-glucose metabolic labelling strategy.

FIG. 2: (c) $^{13}C$ isotopic labelling profile of succinate in the normoxic and ischaemic myocardium. n=4 hearts per group.

FIG. 2: (d) Effect of inhibition of γ-aminobutyric acid (GABA) shunt with vigabatrin on GABA and succinate levels in the ischaemic myocardium. n=3 hearts per group.

FIG. 2: (e) Summary of in silico metabolic modelling of potential drivers of ischaemic succinate accumulation driven by reverse SDH operation; and $^{13}C$-aspartate metabolic labelling strategy to determine the contribution of malate- and adenylosuccinate-linked pathways on ischaemic succinate accumulation.

FIG. 2: (f) Effect of SDH inhibition by dimethyl malonate on succinate accumulation and CAC metabolite abundance in the ischaemic myocardium in vivo. n=3 mice per group.

FIG. 2: (g) Relative ischaemic flux of $^{13}C$-aspartate to the indicated CAC metabolites in the normoxic and ischaemic myocardium. n=4 hearts per group.

FIG. 2: (h) Effect on CAC metabolite abundance in the ischaemic myocardium in vivo of blocking NADH-dependent aspartate entry into the CAC, through aminooxyacetate (AOA)-mediated inhibition of aspartate aminotransferase, or blocking PNC by inhibition of adenylosuccinate lyase with AICAR. n=3 mice per group. * $p<0.05$,  $p<0.01$, * $p<0.001$. Data are shown as the mean±s.e.m of at least three replicates.

FIG. 3: (b) Determination of mitochondrial complex I RET contribution to succinate-driven ROS production at reperfusion through selective inhibition with MitoSNO. n=3 independent cardiomyocyte preparations per group.

FIG. 3: (c) Effect of manipulation of ischaemic succinate levels on NAD(P)H oxidation during late ischaemia and early reperfusion. n=3 independent cardiomyocyte preparations per group.

FIG. 3: (d) Effects of manipulation of ischaemic succinate levels on mitochondrial membrane potential following late ischaemia (left panels) and early reperfusion (right panels) using TMRM fluorescence in de-quench mode (high fluorescence=low membrane potential).

FIG. 3: (e) Effects of manipulation of ischaemic succinate levels on the initial rate of inner membrane re-polarisation following 40 min ischaemia as determined by the rate of TMRM quenching at reperfusion. n=3 independent cardiomyocyte preparations per group.

FIG. 3: (f) Effect of dimethyl succinate and oligomycin on mitochondrial ROS in the aerobic C2C12 myoblasts. Mitochondria within myoblasts under normoxic incubation were hyperpolarised with oligomycin and dimethyl succinate and the rate of MitoSOX oxidation assessed to measure mitochondrial ROS production. n=4 independent experiments of 10-12 myoblasts per trial. * $p<0.05$, ** $p<0.01$. Data are shown as the mean±s.e.m of at least three replicates.

FIG. 4: (b) Representative images of cross-sections from mouse hearts following myocardial infarction±inhibition of ischaemic succinate accumulation by i.v. injection of dimethyl malonate, or reintroduction of ischaemic succinate by i.v. injection of dimethyl malonate and dimethyl succinate. Infarcted tissue is white, the rest of the area at risk is red, and non-risk tissue is dark blue.

FIG. 4: (c) Quantification of myocardial infarct size carried out as described in b. Each open circle represents data from a single mouse, and filled circles represent the mean values of all mice for a particular condition. n=6 mice per group.

FIG. 4: (d) Protection by dimethyl malonate against brain IR injury in vivo. Representative images of cross-sections from rat brains after undergoing tMCAO in vivo with or without treatment with dimethyl malonate. Brains were treated with hematoxylin and eosin to delineate infarcted tissue. Quantification of brain infarct volume FIG. 4: (e) and rostro-caudal infarct distribution FIG. 4: (f) ±dimethyl malonate following brain IR injury by tMCAO in vivo. n=3-6 rats per group.

FIG. 4: (g) Neurological scores for rats following tMCAO±dimethyl malonate. n=3-6 mice per group. * $p<0.05$,  $p<0.01$, * $p<0.001$. Data are shown as the mean±s.e.m, except for (g) for which data are median±C.I.

FIG. 8: (b) Additionally, flux to aKG was determined relative to the proportion of the +5 glutamine pool in the heart. n=4, * p<0.05.

FIG. 12: (b) With oxygen restored complex II metabolised the excess succinate. A delay in regenerating AMP to ADP, as typified in the first minute of reperfusion, limited the flux through ATP-synthase. This in turn prevented complex III consuming all the ubiquinol generated by complex II, as the membrane became hyper-polarised. The excess flux of ubiquinol and protons forced complex I to run in reverse, which would generate ROS.

FIG. 12: (c) Once the flux of succinate was reduced to normal levels, as in the transition from late reperfusion to normoxia, the fluxes through the respiratory chain and citric acid cycle returned to normal.

FIG. 13: Tracking cardiomyocytes ROS levels in primary cardiomyocytes during in situ IR. Primary rat cardiomyocytes were subjected to 40 min ischaemia and reoxygenation with ROS levels tracked throughout the experiment by ratiometric measurement of dihydroethidium (DHE) oxidation. Ischaemic buffer contained either no additions, 4 mM dimethyl malonate, or 4 mM dimethyl succinate. Representative traces of each condition are shown. The highlighted window indicates the period of the experiment expanded in detail in FIG. 3.a.

FIG. 15: (b) TMRM signal during the transition from ischaemia to reoxygenation. n=3-4 experiments from independently isolated primary rat cardiomyocytes per group.

DESCRIPTION OF THE EMBODIMENTS

Figure 1:
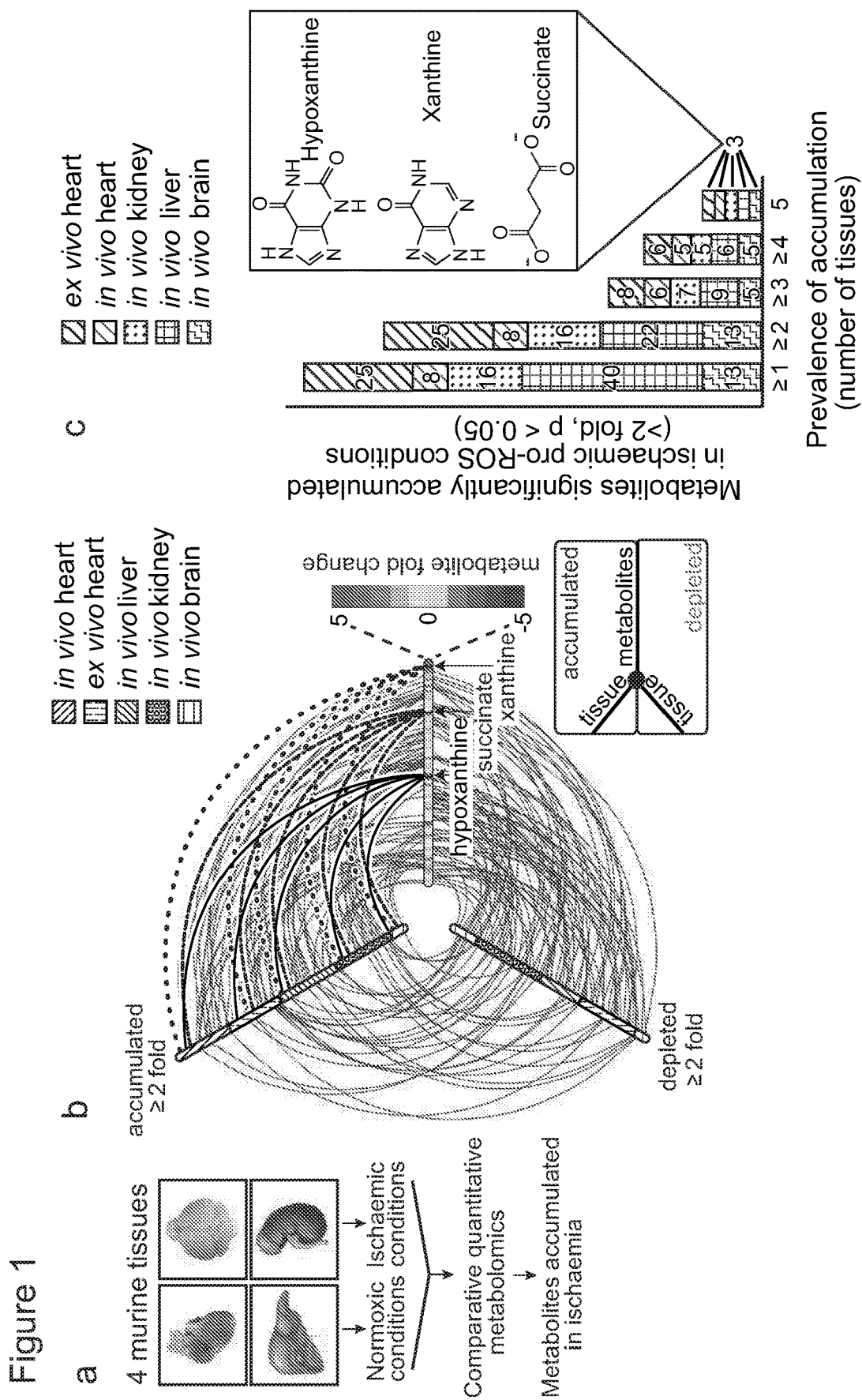
FIG. 1: Comparative metabolomics identifies succinate as a potential mitochondrial metabolite that drives reperfusion ROS production. (a) Outline of comparative metabolomics strategy for identification of metabolites that accumulate in vivo under ischaemic conditions.
Figure 1:
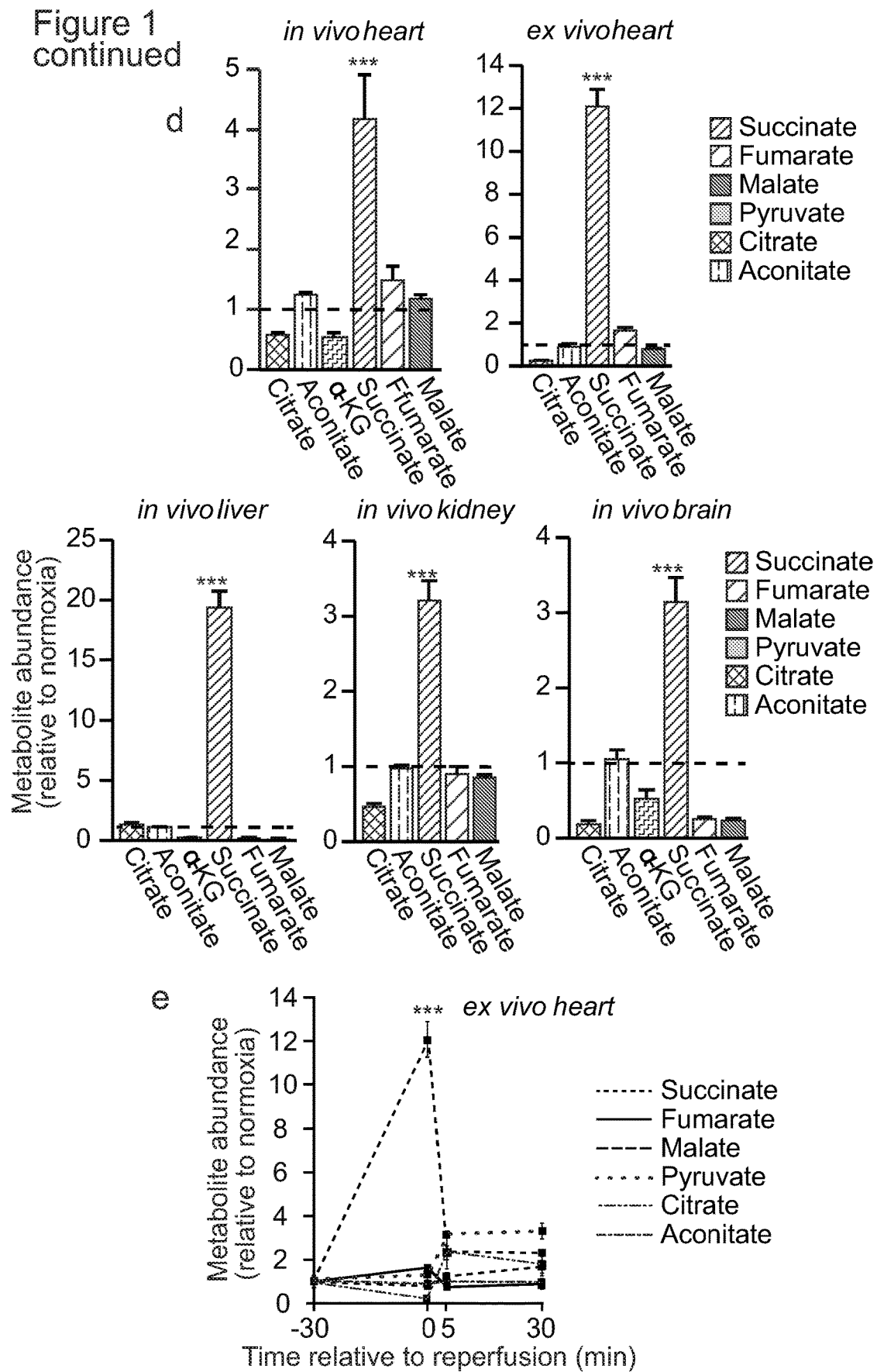

Mitochondrial ROS production is a critical early driver of ischaemia-reperfusion (IR) injury, but has been considered a non-specific consequence of the interaction of a dysfunctional respiratory chain with oxygen during reperfusion[1-4]. The inventors investigated an alternative hypothesis: that mitochondrial ROS during IR are generated by a specific metabolic process. To do this the inventors developed a comparative metabolomics approach to identify conserved metabolic signatures in tissues during IR that might indicate the source of mitochondrial ROS (FIG. 1a). Liquid chromatography-mass spectrometry (LC-MS)-based metabolomic analysis of murine brain, kidney, liver and heart subjected to ischaemia in vivo (FIG. 1a) revealed changes in several metabolites. However, only three were elevated across all tissues (FIG. 1b, c and Table 1).

Various murine tissues exposed to sufficient periods of ischaemia to prime for reperfusion ROS production were subjected to metabolomic analysis and comparison

TABLE 1

Full comparative analysis of metabolites significantly accumulated in ischaemic pro-ROS conditions.

| Prevalence of accumulation (number of tissues) | Metabolites significantly accumulated in ischaemic pro-ROS conditions (>2 fold, p < 0.05) | Tissue |
| --- | --- | --- |
| 5 | Succinate | All |
| 5 | Xanthine | All |
| 5 | Hypoxanthine | All |
| 4 | Adenine | B, L, K, H |
| 4 | Propionylcarnitine | B, L, H, HL |
| 4 | Guanine | L, K, H, HL |
| 3 | Lactate | L, K, H |
| 3 | Choline | L, K, HL |
| 3 | Proline | L, K, H |
| 2 | Allopurinol | B, H |
| 2 | Uracil | B, H |
| 2 | Adenylsuccinate | B, H |
| 2 | Cysteine | B, L |
| 2 | Cytosine | B, H |
| 2 | Creatinine | B, L |
| 2 | Stearoylcarnitine | L, K |
| 2 | Phenylalanine | L, K |
| 2 | Lysine | L, K |
| 2 | Ornithine | L, K |
| 2 | Tryptophan | L, K |
| 2 | Leucine | L, K |
| 2 | AMP | L, H |
| 2 | Asparagine | L, K |
| 2 | Arginine | L, K |
| 2 | Palmitoylcarnitine | L, HL |
| 2 | Adenosine | L, HL |
| 1 | Uridine | L |
| 1 | N-AcetylAspartate | L |
| 1 | Tyrosine | L |
| 1 | Phosphorylcholine | L |
| 1 | Acetate | L |
| 1 | Methionine | L |
| 1 | OleylCarnitine | L |
| 1 | Threonine | L |
| 1 | 2-hydroxyglutarate | L |
| 1 | Valine | L |
| 1 | Glucose | L |
| 1 | Alanine | L |
| 1 | GlycerolPhosphate | L |
| 1 | Glycerylphosphorylcholine | L |
| 1 | AcetylCholine | L |
| 1 | Carnitine | L |

B = brain,
H = whole heart ischaemia ex vivo,
HL = LAD ischaemia in vivo,
K = kidney,
L = liver Two metabolites were well-characterised by-products of ischaemic purine nucleotide breakdown, xanthine and hypoxanthine[6], corroborating the validity of our approach. Xanthine and hypoxanthine are metabolised by cytosolic xanthine oxidoreductase and do not contribute to mitochondrial metabolism[7]. The third metabolite, the mitochondrial citric acid cycle (CAC) intermediate succinate, increased 3- to 19-fold across the tested tissues (FIG. 1d) and was the sole mitochondrial metabolic feature of ischaemia that occurred universally in a range of metabolically diverse tissues. Therefore the inventors focused on the potential role of succinate in mitochondrial ROS production during IR.

Figure 5:
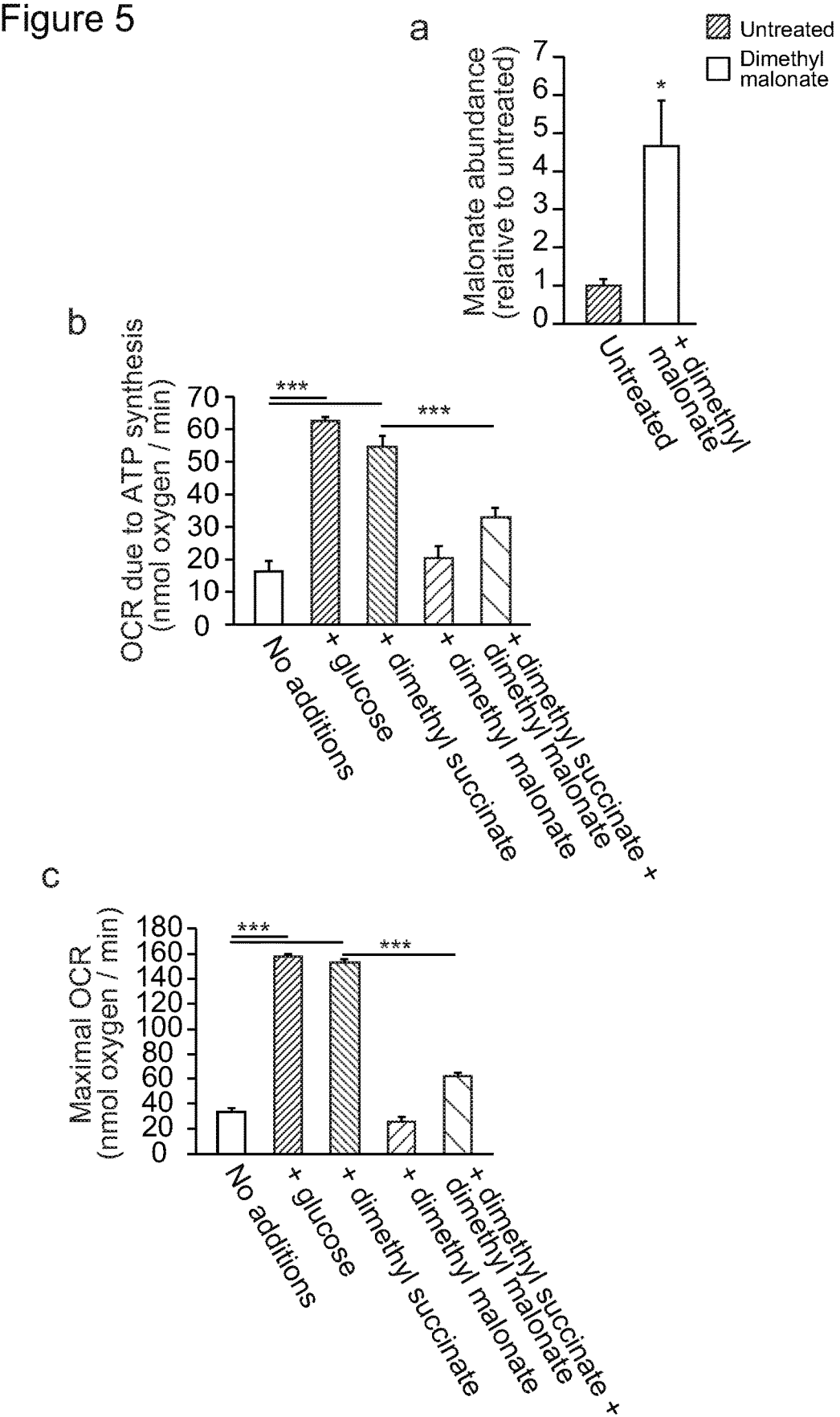
FIG. 5: Dimethyl malonate and dimethyl succinate treatment of cells and in vivo results in intracellular accumulation of malonate and succinate. a, Intravenous infusion of dimethyl malonate in vivo results in accumulation of malonate in the ischaemic myocardium. b, C2C12 cells were incubated with: no additions, glucose, 5 mM dimethyl succinate, 5 mM dimethyl malonate, or 5 mM dimethyl malonate and 5 mM dimethyl succinate. Cellular oxygen consumption rate due to ATP synthesis and c, maximal rates were determined using a Seahorse XF96 analyser. n=3-4, *, $p<0.05$; ***, $p<0.001$.

Since mitochondrial ROS production occurs early in reperfusion[1-4,8,9], it follows that metabolites fuelling ROS should be oxidised quickly. Strikingly, the succinate accumulated during ischaemia was restored to normoxic levels by 5 minutes reperfusion ex vivo in the heart (FIG. 1e), and this was also observed in vivo in the heart, brain and kidney (FIG. 1f-h). Furthermore, these succinate changes were localised to areas of the tissues where IR injury occurred in vivo, and took place in the absence of the accumulation of other CAC metabolites (FIG. 1d, f). To further assess the role of succinate in driving ROS production, the inventors administered a cell permeable derivative of succinate, dimethyl succinate (FIG. 5), to ischaemic primary cardiomyocytes[8] and found that this significantly increased mitochondrial ROS production during reperfusion (FIG. 1i). These data suggest that the succinate accumulated during ischaemia then fuels ROS production upon reperfusion.

Figure 2:
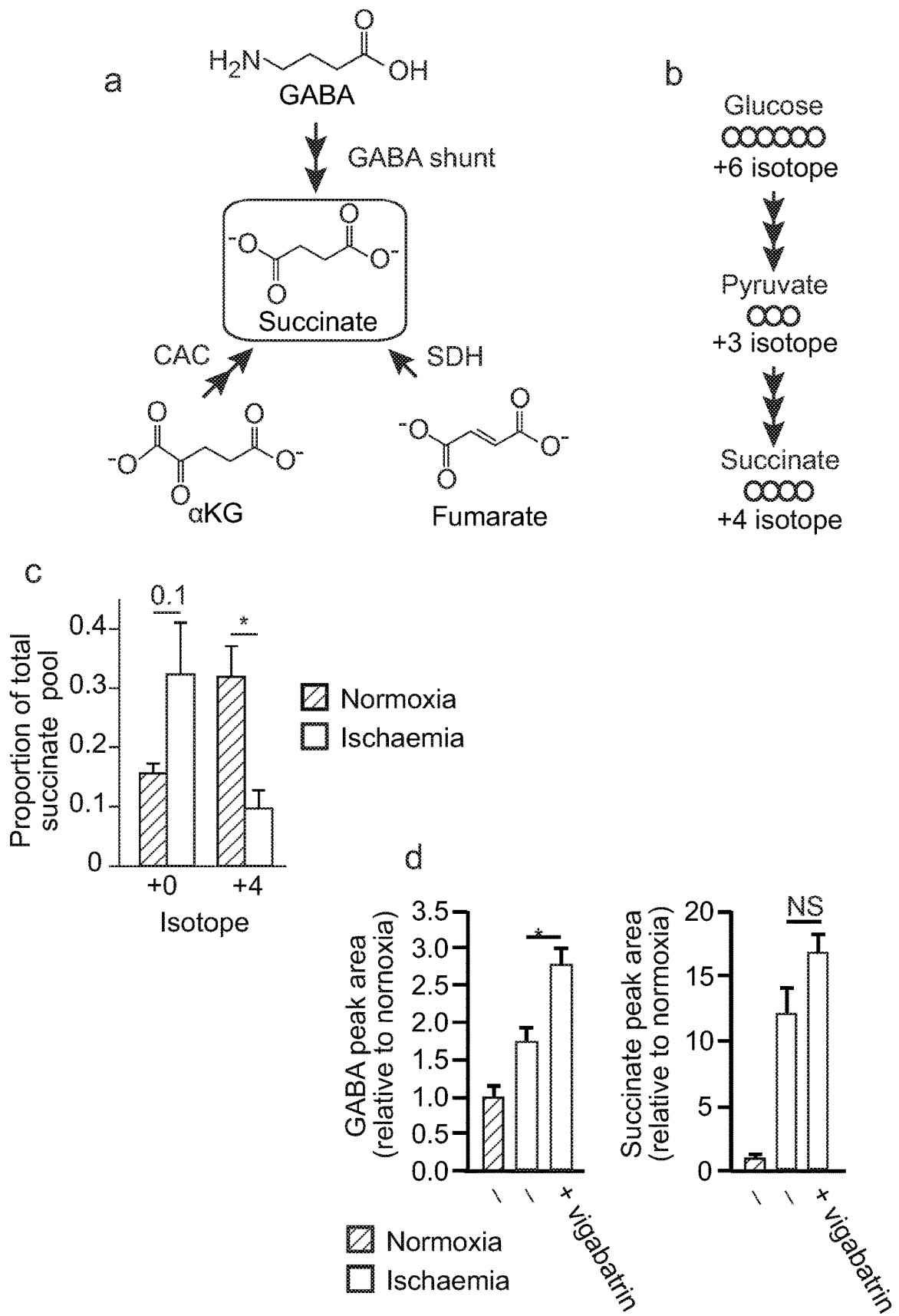
FIG. 2: Reverse SDH activity drives ischaemic succinate accumulation by the reduction of fumarate produced by the malate-aspartate shuttle and the purine nucleotide cycle. (a) Potential inputs to succinate-directed ischaemic flux.
Figure 2:
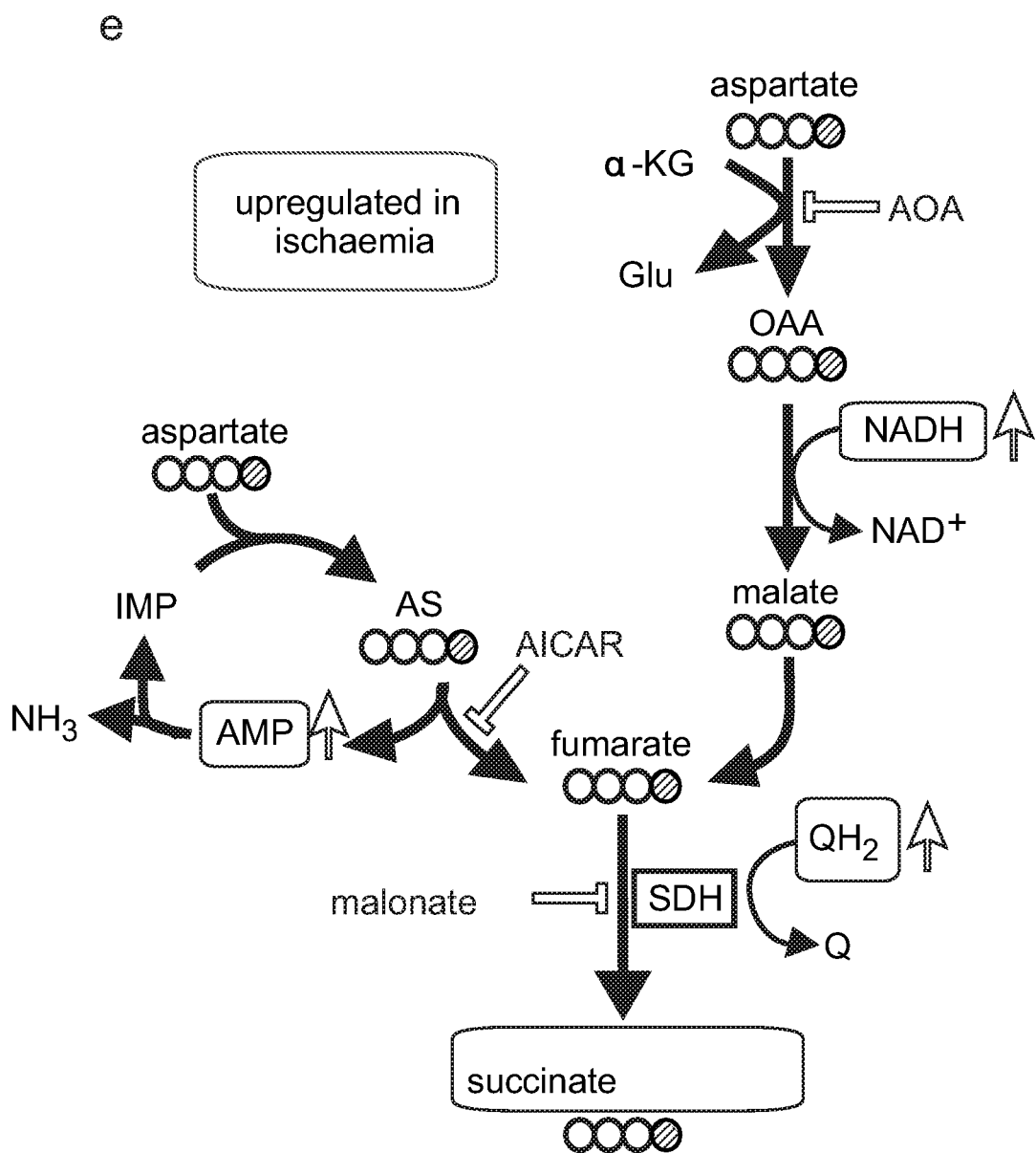
Figure 2:
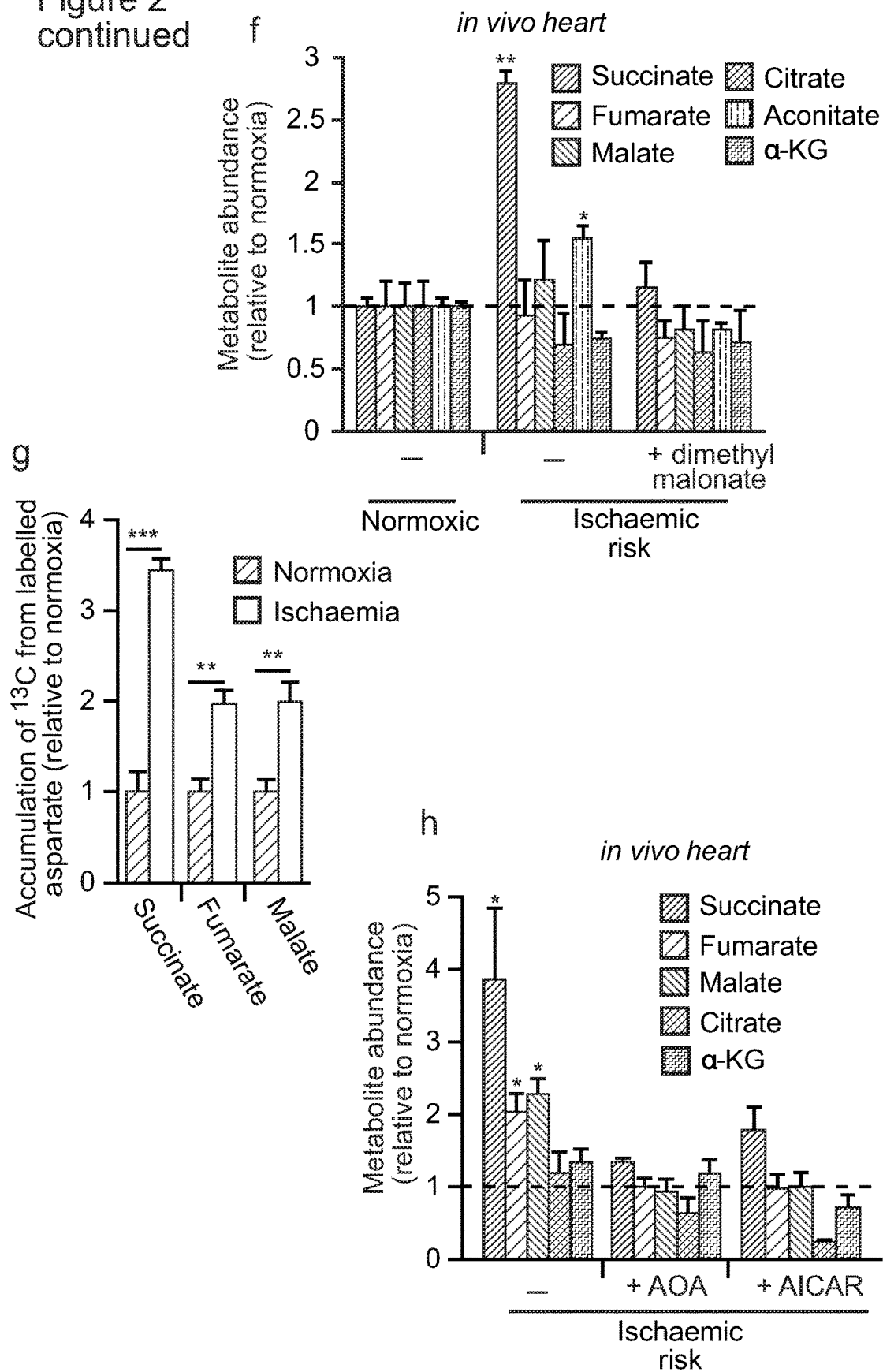
Figure 8:
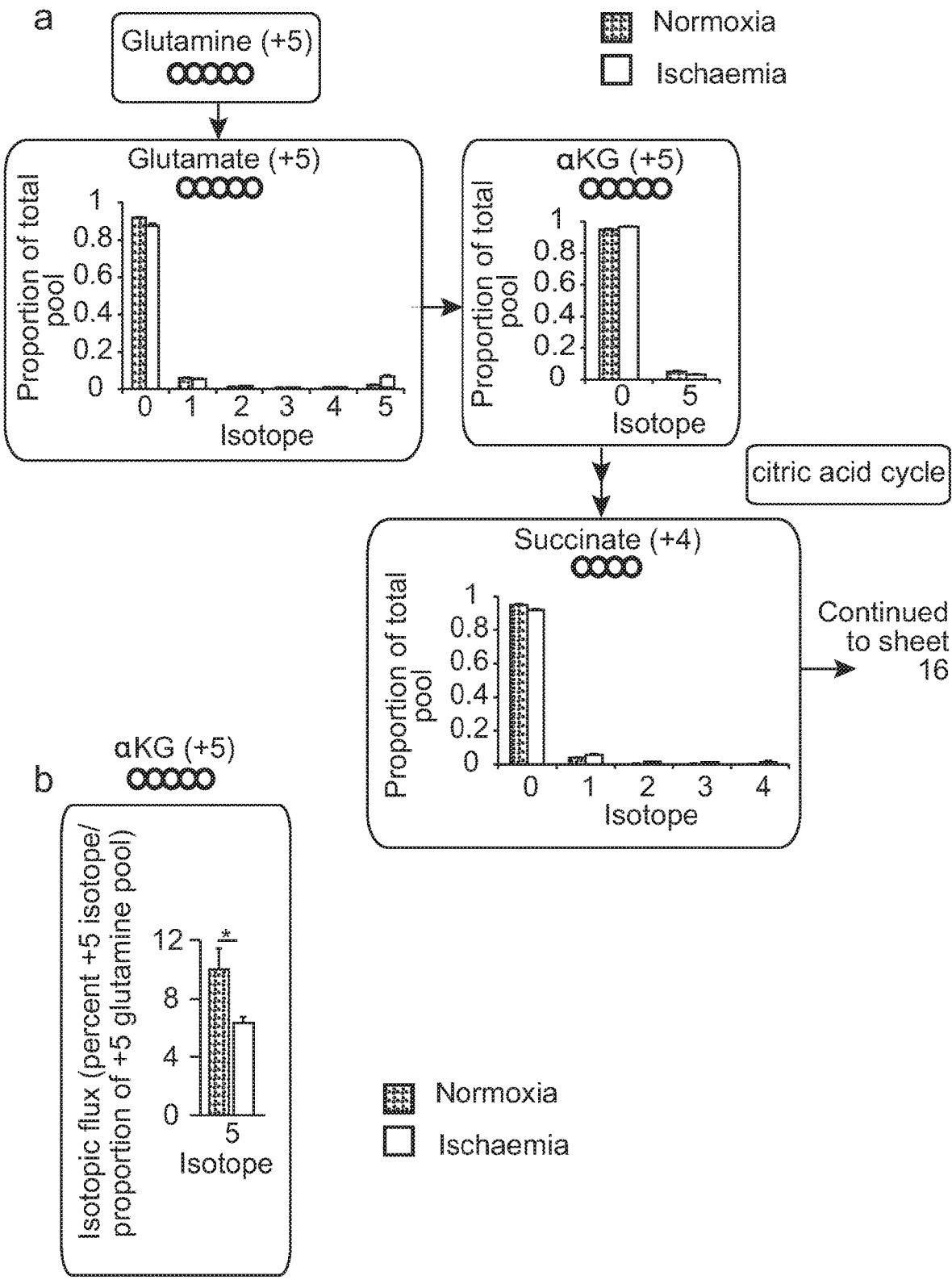
FIG. 8: Metabolic labelling of CAC and proximal metabolites by 13C glutamine in the ischaemic and normoxic myocardium. Isotopic flux from glutamine to CAC and proximal metabolites during normoxic and ischaemic myocardial respiration. Mouse hearts were perfused with 4 mM 13C glutamine (+5 labelled) for to min followed by either 30 min no flow ischaemia or 30 min normoxic respiration followed by snap freezing and metabolomics analysis. (a) The isotopic profile for each metabolite is expressed as a proportion of the total pool.
Figure 8:
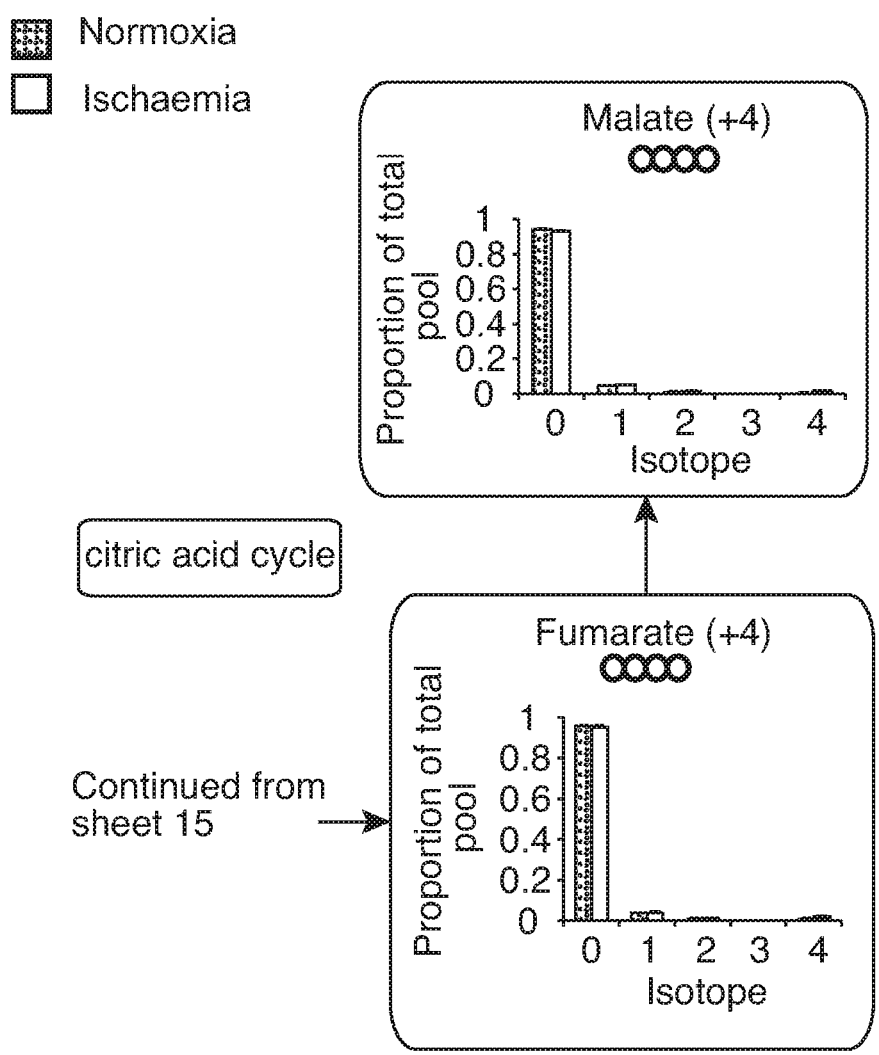
Figure 9:
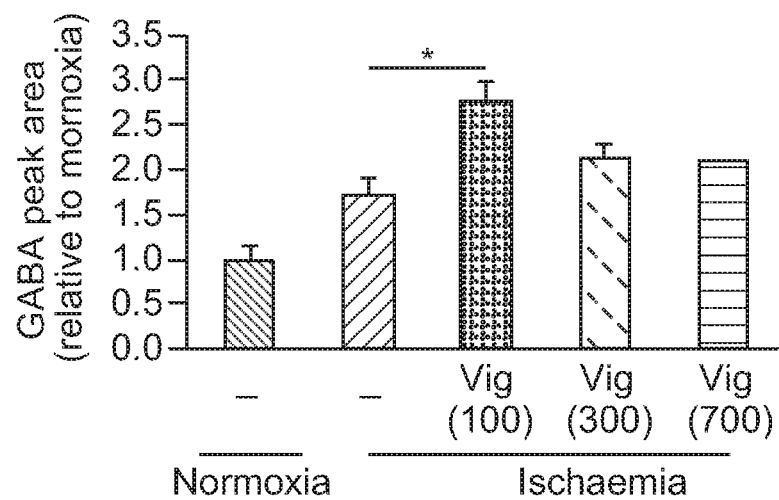
FIG. 9: Effect of GABA transaminase inhibition by vigabatrin on GABA shunt and CAC metabolites in the ischaemic myocardium. Perfused mouse hearts were subjected to 30 min no flow ischaemia±continuous infusion of vigabatrin (Vig; 100, 300, and 700 µM) 10 min prior to ischaemia. Heart tissue was snap frozen and a, GABA and b, succinate abundance quantified relative to normoxic levels by LC-MS. n=3, * p<0.05.
Figure 9:
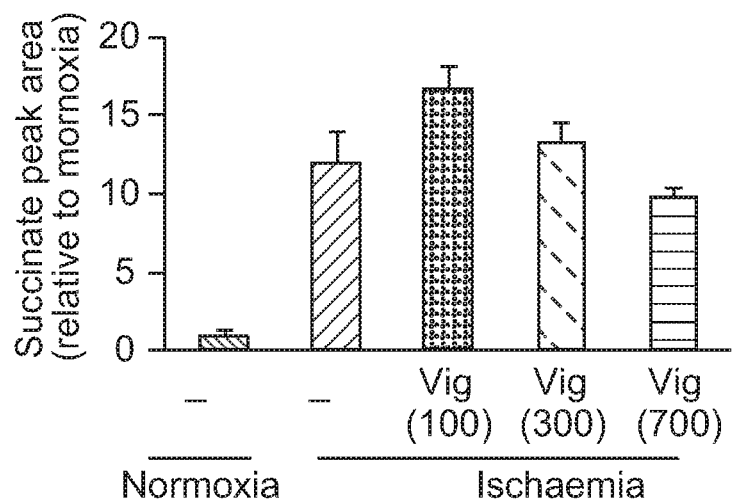

To determine the mechanisms responsible for succinate accumulation during ischaemia and explore its role in IR injury the inventors focused on the heart, because of the many experimental and theoretical resources available. In mammalian tissues succinate can be generated through α-ketoglutarate-dependent CAC flux from pyruvate or glutamate, or the γ-aminobutyric acid (GABA) shunt, (FIGS. 2a and 6)[10,11]. Ischaemic CAC flux to succinate via α-ketoglutarate was investigated by measuring its isotopologue distribution following infusion with $^{13}$C-labelled glucose or glutamine, which enter the CAC from pyruvate and glutamate, respectively. The $^{13}$C-isotopologue distribution of succinate upon perfusion with U-$^{13}$C-glucose was significantly reduced in ischaemic hearts indicating that pyruvate and α-ketoglutarate-linked CAC flux to succinate decreases during ischaemia (FIGS. 2b, c, and 7). Glutamine was not a major carbon source for CAC metabolites in normoxia or ischaemia (FIG. 8a). Furthermore, the minimal $^{13}$C-glutamine incorporation to α-ketoglutarate observed was decreased in ischaemia (FIG. 8b), and inhibition of the GABA shunt with vigabatrin[10] did not decrease ischaemic succinate accumulation (FIGS. 2d and 9). Therefore the build up of succinate during ischaemia is not caused by conventional operation of cardiac metabolism.

Figure 10:
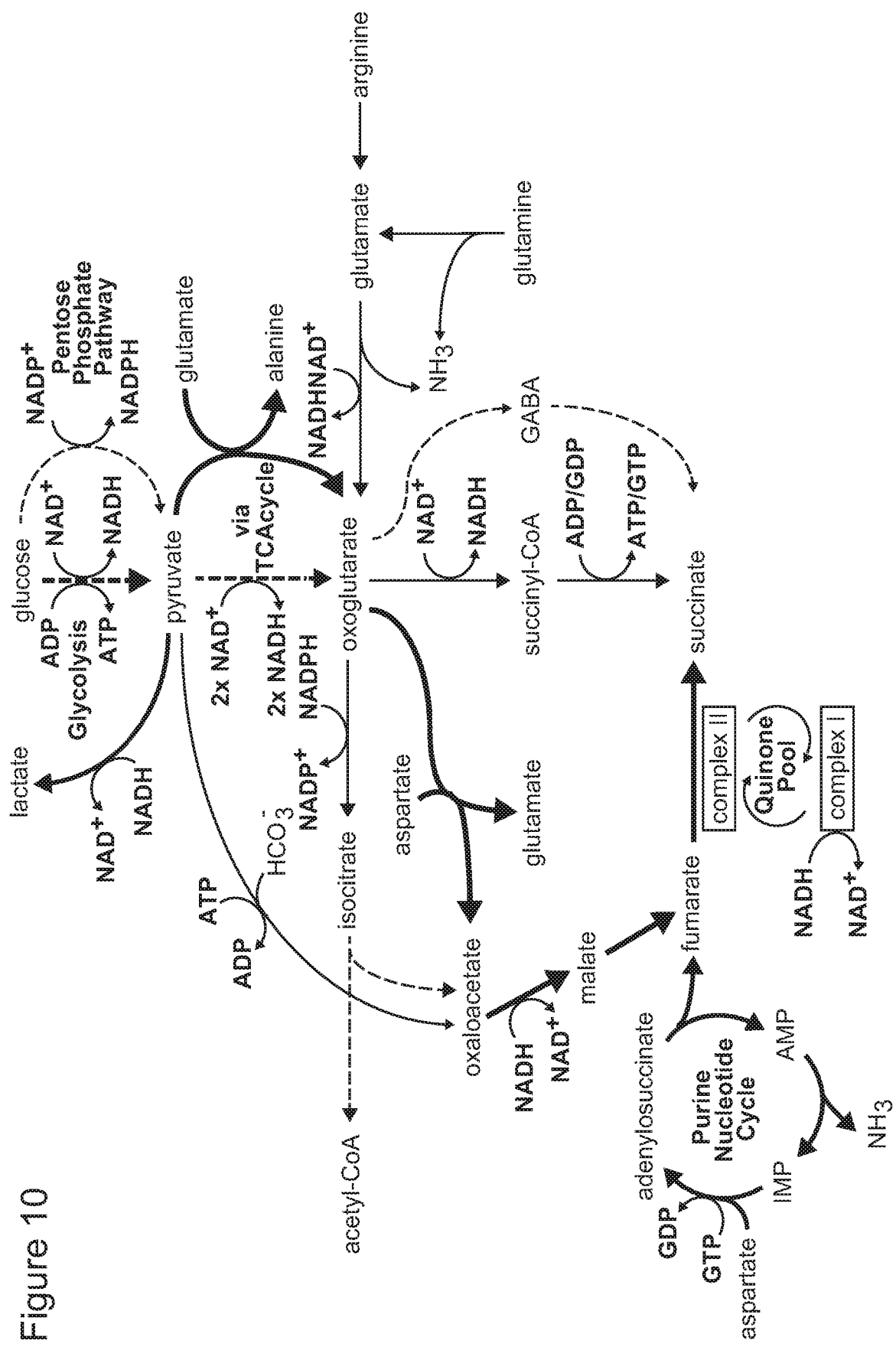
FIG. 10: Unabridged metabolic model identifying pathways that can become activated by tissue ischaemia to drive succinate accumulation. To identify the metabolic pathways that could contribute to succinate production under ischaemia, we simulated these conditions using flux balance analysis in conjunction with an expanded version of the iAS253 mitochondrial model of central cardiac metabolism. The major pathways contributing to succinate accumulation (bold red lines) were via fumarate feeding into the reverse activity of SDH. This was produced by the purine nucleotide cycle (PNC) and the malate-aspartate shuttle (MAS), which consumed glucose and aspartate, and also led to significant production of lactate and alanine. Lesser sources of succinate (thin red lines) included glycolysis and glutaminolysis but this was relatively minor as this route was constrained by the overproduction of NADH. In addition a small amount of fumarate was generated by pyruvate carboxylase activity. The GABA shunt did not contribute (black dashed line).

To explore other mechanisms that could lead to succinate accumulation during ischaemia, the inventors considered whether during anaerobic metabolism SDH might act in reverse to reduce fumarate to succinate[12-14]. While SDH reversal has not been demonstrated in ischaemic tissues, in silico flux analysis determined succinate production by SDH reversal during ischaemia as an optimal solution (FIGS. 2e and 10). This approach also suggested that fumarate supply to SDH could come from two converging pathways: the malate/aspartate shuttle (MAS), where the high NADH/NAD ratio drives malate formation that is converted to fumarate[14-16]; and AMP-dependent activation of the purine nucleotide cycle (PNC) that drives fumarate production[17,18] (FIGS. 2e and 10). To test this prediction experimentally, the inventors infused mice with dimethyl malonate, a membrane-permeable precursor of the SDH competitive inhibitor malonate (FIG. 5)[19,20]. Surprisingly, dimethyl malonate infusion strikingly decreased succinate accumulation in the ischaemic myocardium (FIG. 2f). This result indicates that SDH operates in reverse in the ischaemic heart, as inhibition of SDH operating in its conventional direction would have further increased succinate (FIGS. 2a and 10). Therefore succinate accumulates during ischaemia from fumarate reduction by the reversal of SDH.

Figure 6:
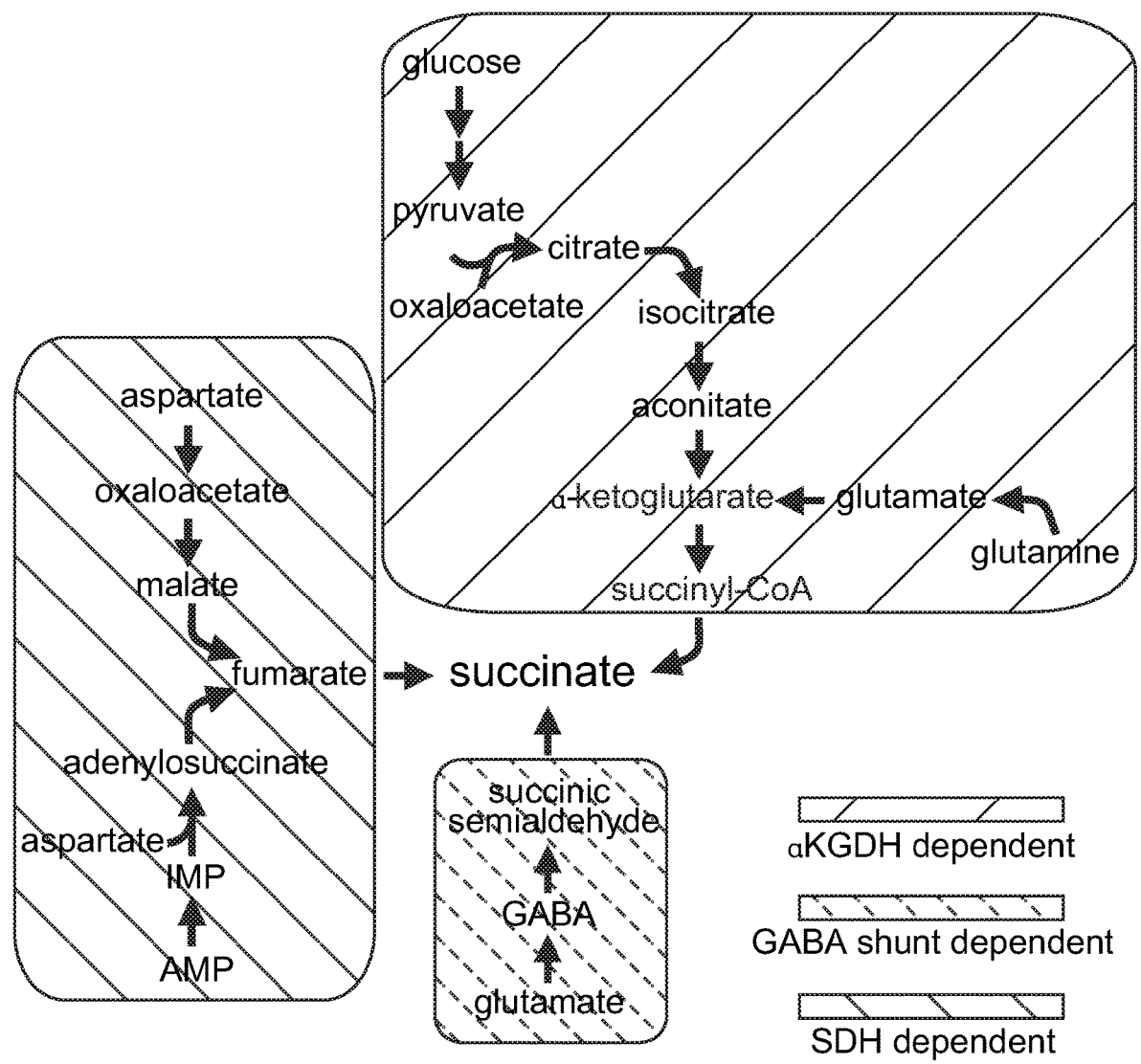
FIG. 6: Summary of the three potential metabolic inputs for succinate-directed ischaemic flux. To understand the metabolic pathways that could contribute to succinate production under ischaemia, an updated version of the iAS253 model of cardiac metabolism was employed to simulate ischaemia using flux balance analysis. The model showed three possible mechanisms for producing succinate: from alpha-ketoglutarate produced by the CAC, derived from glycolysis and glutaminolysis (grey box), from succinic semialdehyde produced from the GABA shunt (blue box), and from fumarate produced from the malate-aspartate shuttle and purine nucleotide cycle (red box) via the reversal of SDH.
Figure 7:
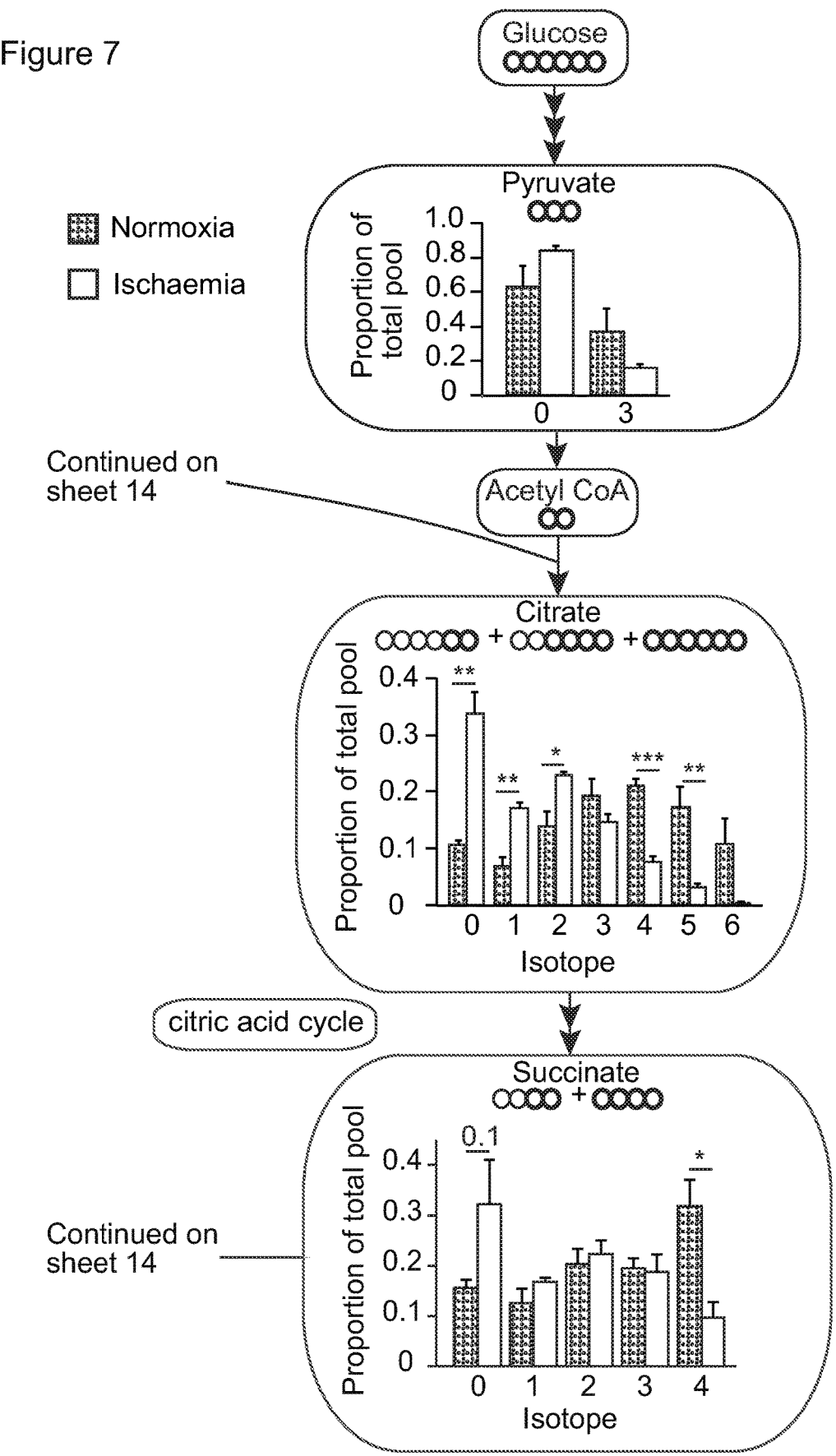
FIG. 7: Metabolic labelling of CAC and proximal metabolites by 13C glucose in the ischaemic and normoxic myocardium. Proportional isotopic labelling profile of CAC and proximal metabolites during normoxic and ischaemic myocardial respiration. Mouse hearts were perfused with 11 mM 13C glucose for 10 min followed by either 30 min no flow ischaemia or 30 min normoxic respiration followed by snap freezing and LC-MS metabolite analysis. n=4, * P<0.05,  p<0.01, * p<0.001.
Figure 7:
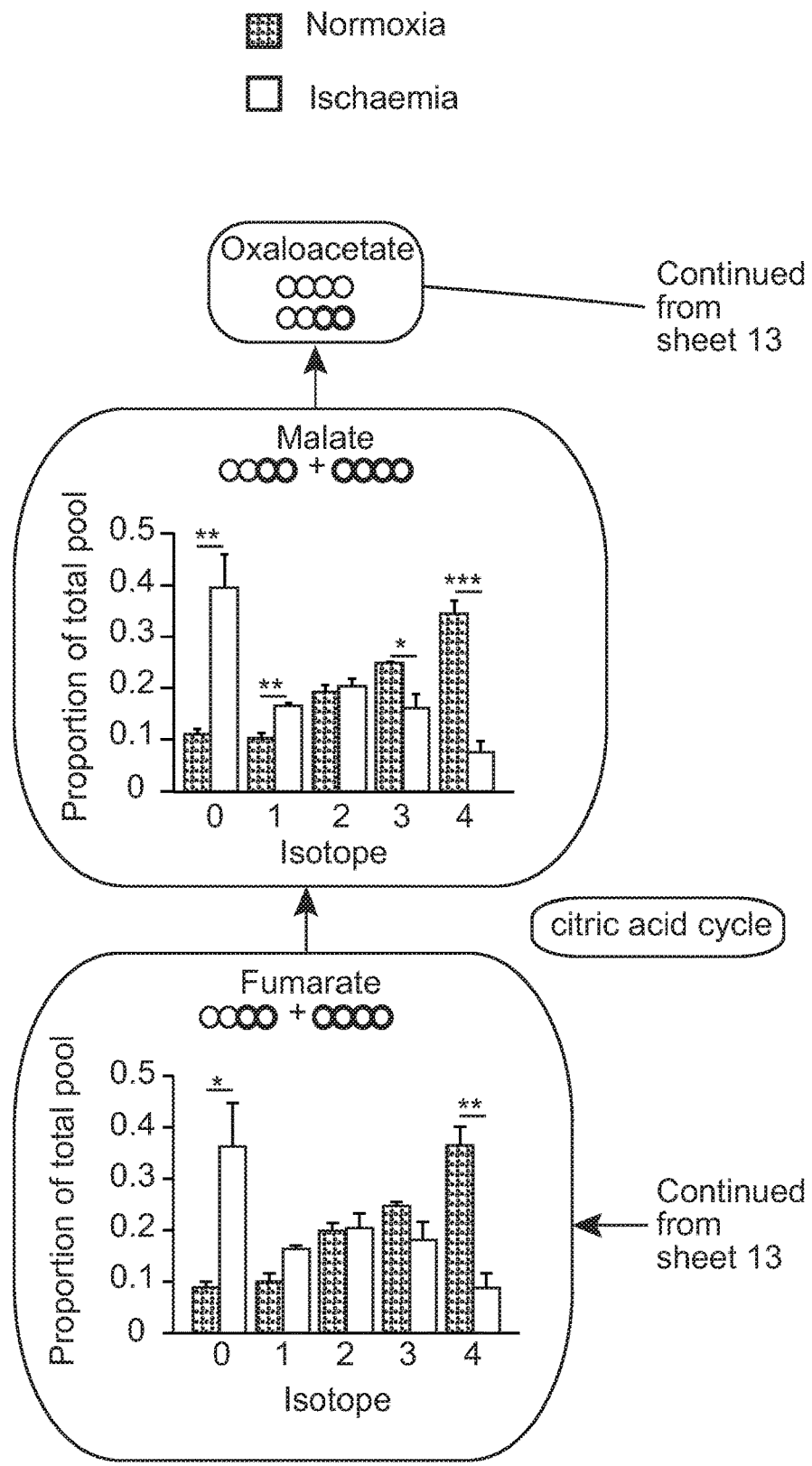
Figure 11:
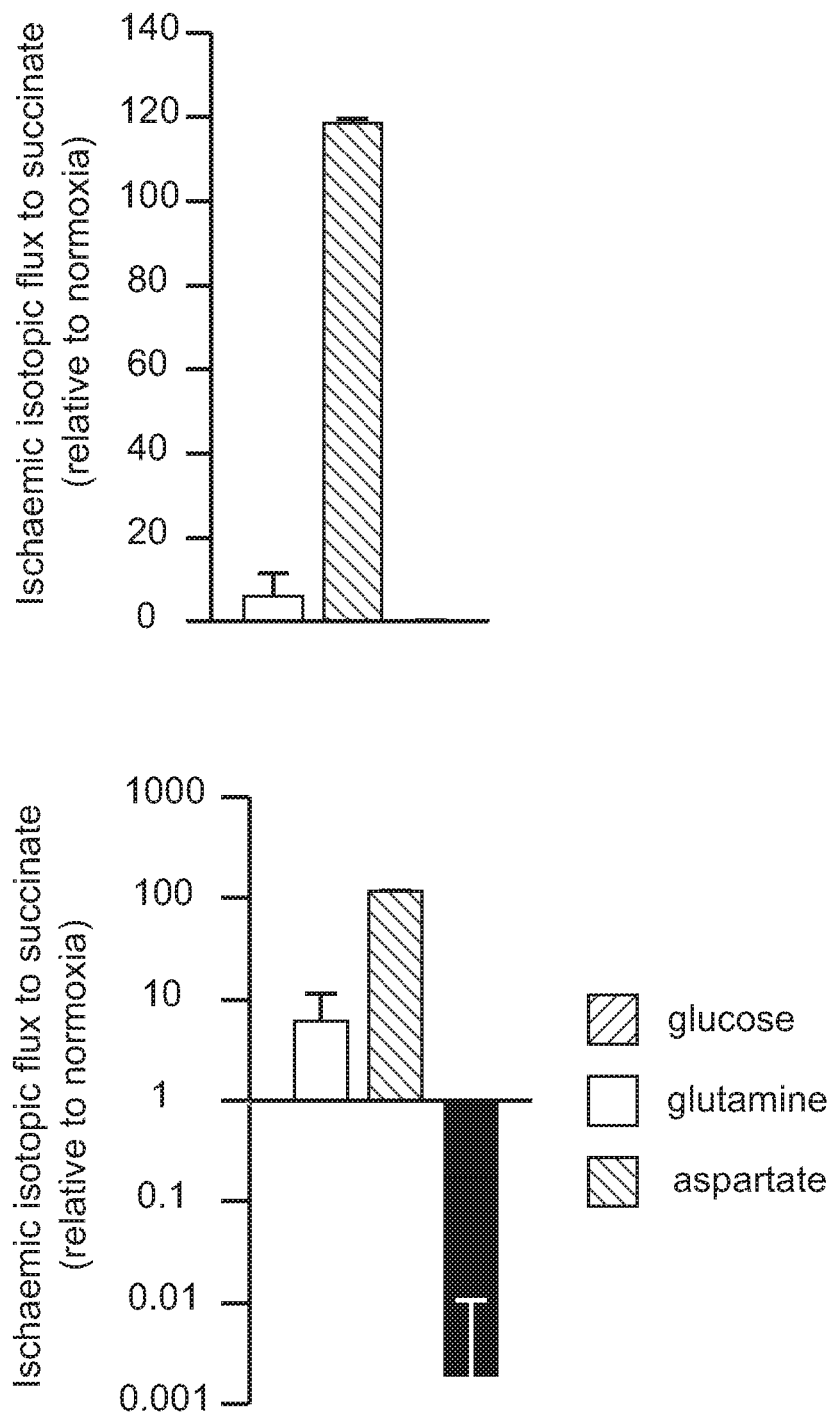
FIG. 11: Comparison of 13C ischaemic metabolite fluxes to succinate relative to isotopic pools. Mouse hearts were perfused with 13C-glucose (+6 labelled), 13C-glutamine (+5 labelled), or 13C-aspartate (+1 labelled) for 10 min followed by 30 min no flow ischaemia or 30 min normoxic respiration, and snap freezing and metabolomics analysis. To compare the relative magnitude of metabolite flux from each carbon source, ischaemic 13C incorporation to succinate compared to the unlabelled succaainate pool was determined relative to normoxia, and expressed relative to the total labelled pool of 13C-infused precursor. Data are plotted on a linear (left) and logarithmic (right) scale.

Since aspartate is a common carbon source for fumarate in both the PNC and the MAS pathways (FIG. 2e), the inventors used $^{13}$C-labelled aspartate to evaluate the contribution of these pathways to succinate production during ischaemia (FIGS. 6 and 10). $^{13}$C-aspartate infusion significantly increased $^{13}$C-succinate content of the ischaemic myocardium compared to normoxia (FIG. 2g). In fact, $^{13}$C-asparate was the only $^{13}$C-carbon donor that incorporated significantly into succinate during ischaemia (FIG. 11). To characterise the relative contributions of the MAS and PNC to ischaemic succinate accumulation the inventors used aminooxyacetate (AOA), which inhibits aspartate aminotransferase in the MAS[21] (FIG. 2e) and 5-amino-1-β-D-ribofuranosyl-imidazole-4-carboxamide (AICAR), which inhibits adenylosuccinate lyase in the PNC[18,22] (FIG. 2e). Both inhibitors decreased ischaemic succinate levels (FIG. 2h). Therefore, these results indicate that during ischaemia both the MAS and PNC pathways increase fumarate production, which is then converted to succinate by SDH reversal.

Figure 3:
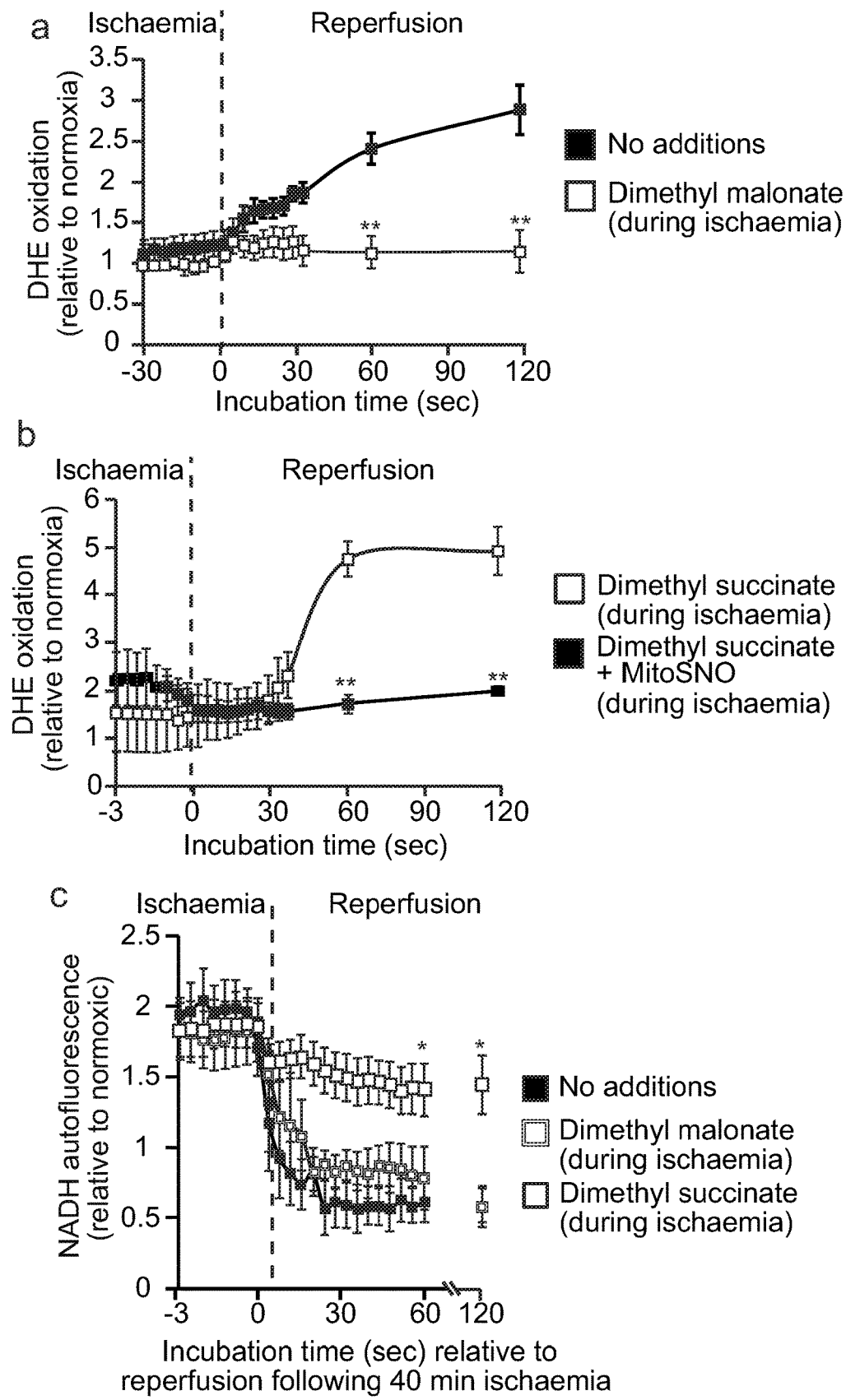
FIG. 3: Ischaemic succinate levels control ROS production, mitochondrial membrane polarisation, and NAD(P)H reduction state at reperfusion in adult primary cardiomyocytes. (a) Effect of manipulation of ischaemic succinate levels on ROS production measured as DHE oxidation during late ischaemia and early reperfusion. n=3 independent cardiomyocyte preparations per group.
Figure 3:
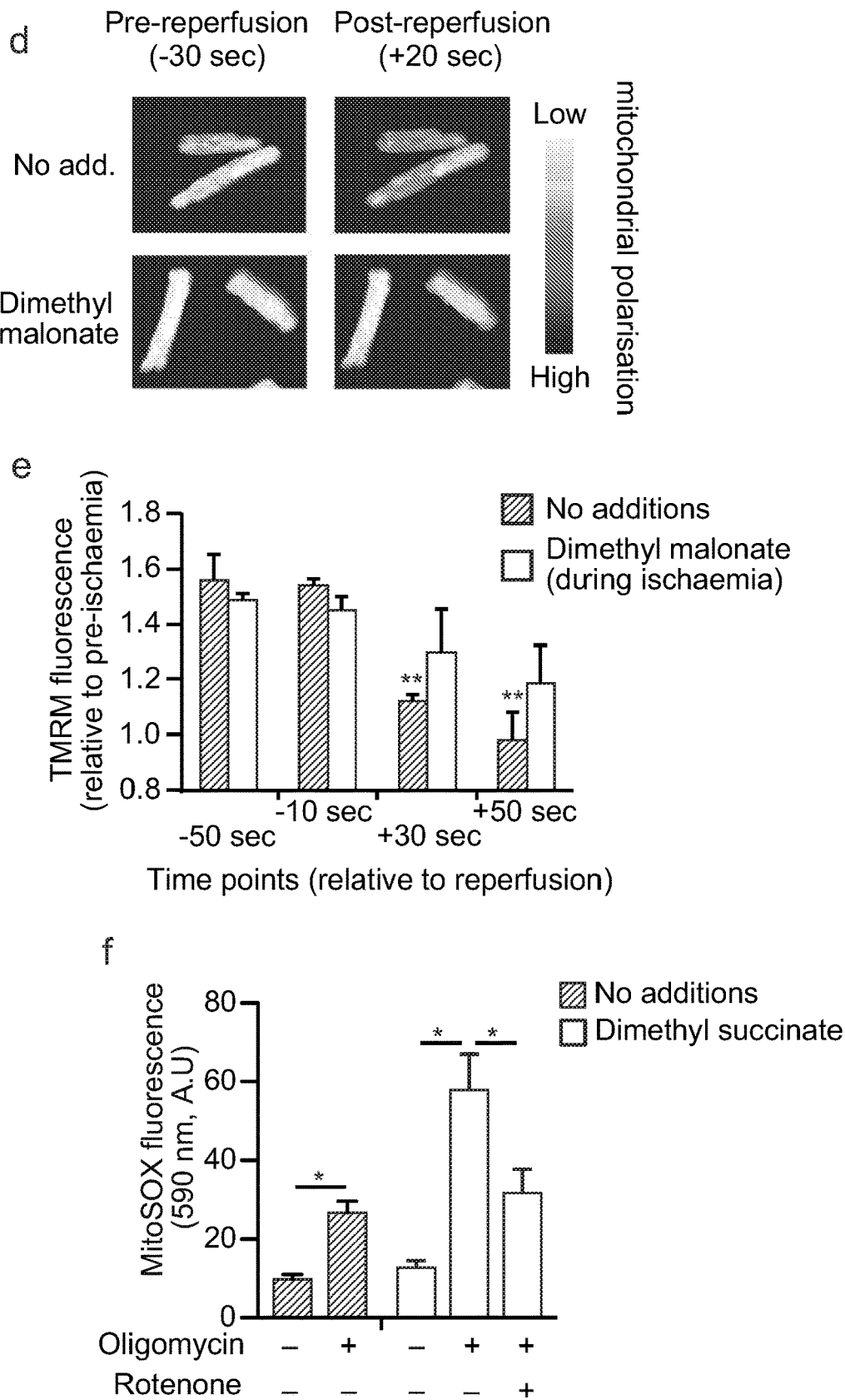
Figure 12:
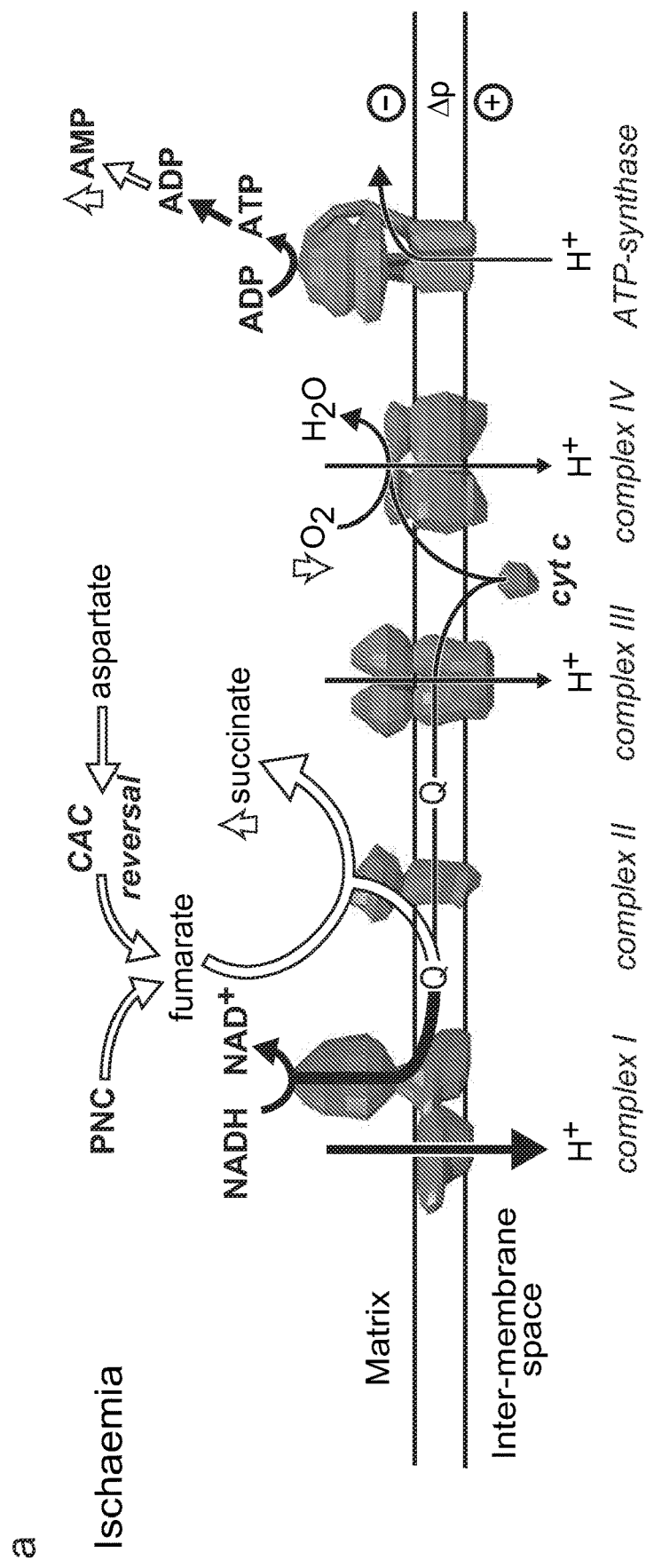
FIG. 12: Predicted changes in pathways of succinate and OXPHOS metabolism during ichaemia and following reperfusion. To determine possible changes in succinate metabolism during ischaemia, reperfusion and normoxia, cardiac metabolism was simulated in these conditions using an expanded version of the iAS253 model with flux balance analysis. The simulations predicted that: (a) under ischaemia, complex II ran in reverse by using ubiquinol produced by complex I to reduce fumarate to succinate, thereby acting as a terminal electron acceptor instead of oxygen. Fumarate was produced from the purine nucleotide cycle (PNC) and reversal of the citric acid cycle (CAC). Flux through the rest of the respiratory chain was diminished and AMP was produced from ADP due to insufficient ATP production.
Figure 12:
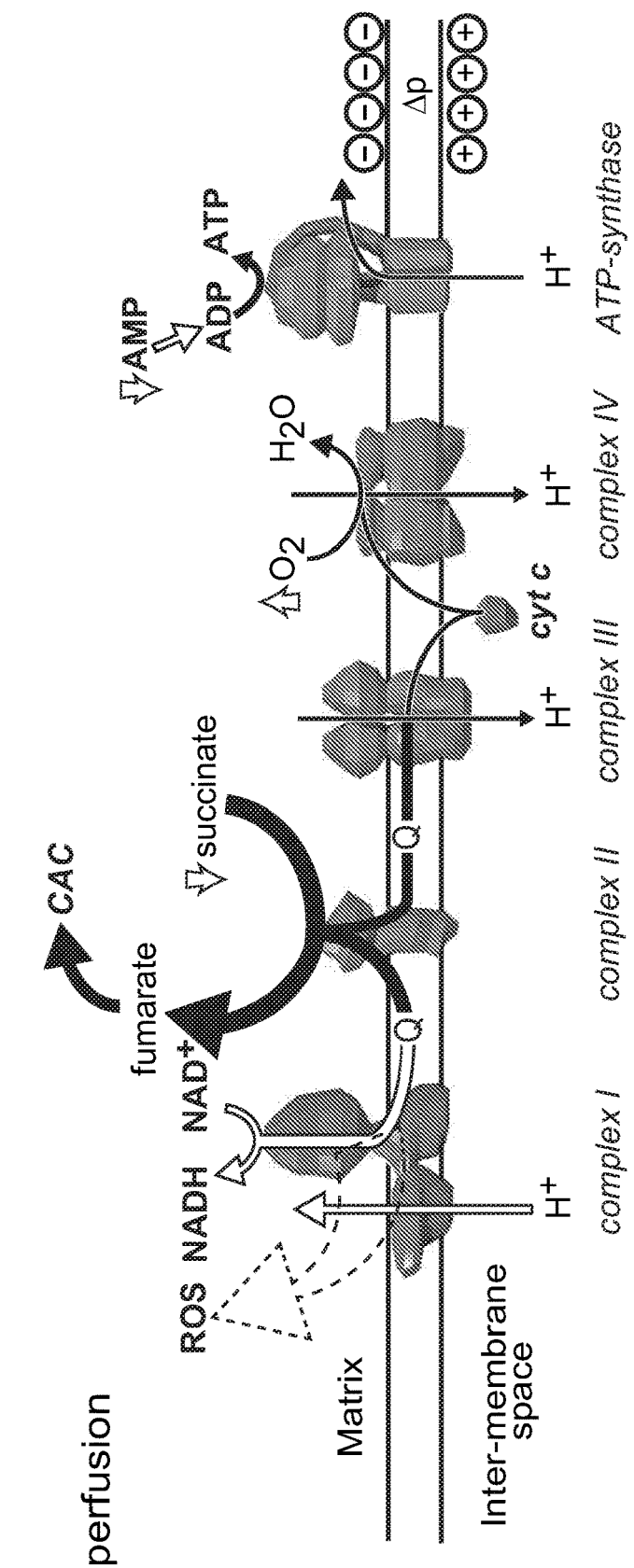
Figure 12:
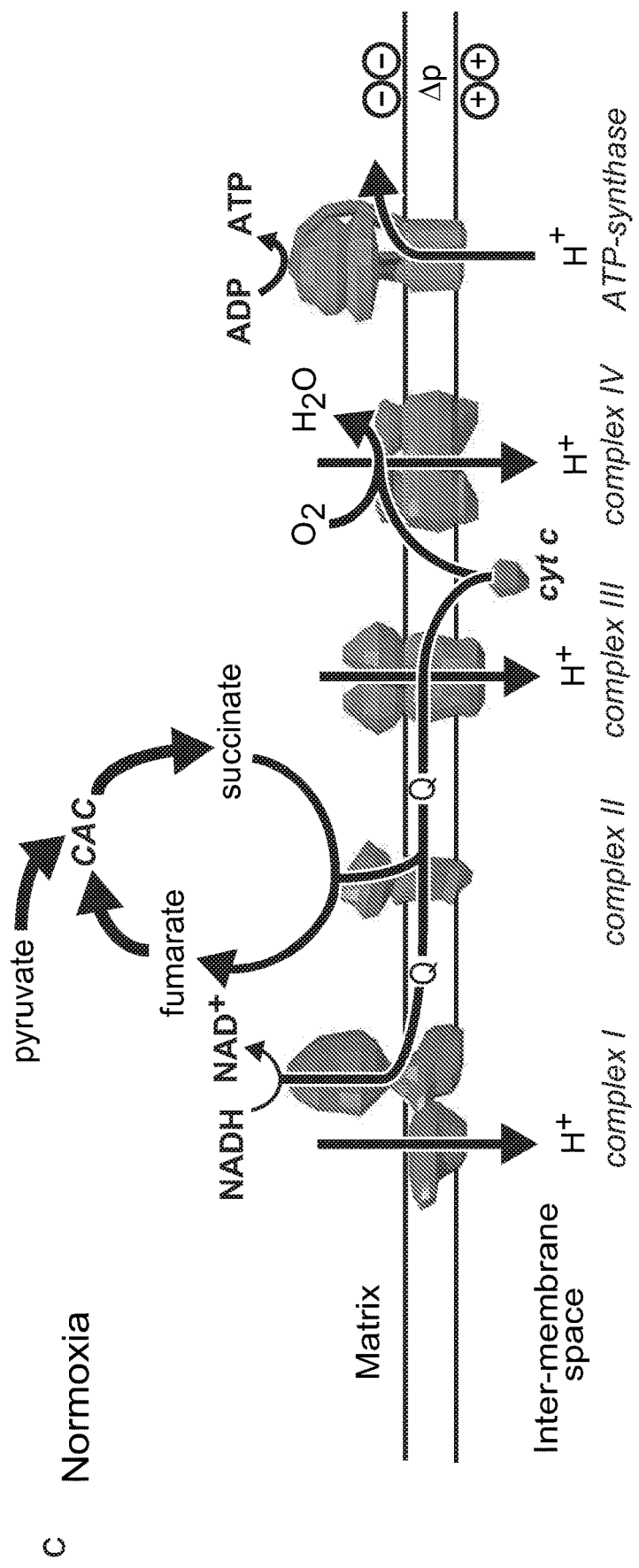
Figure 13:
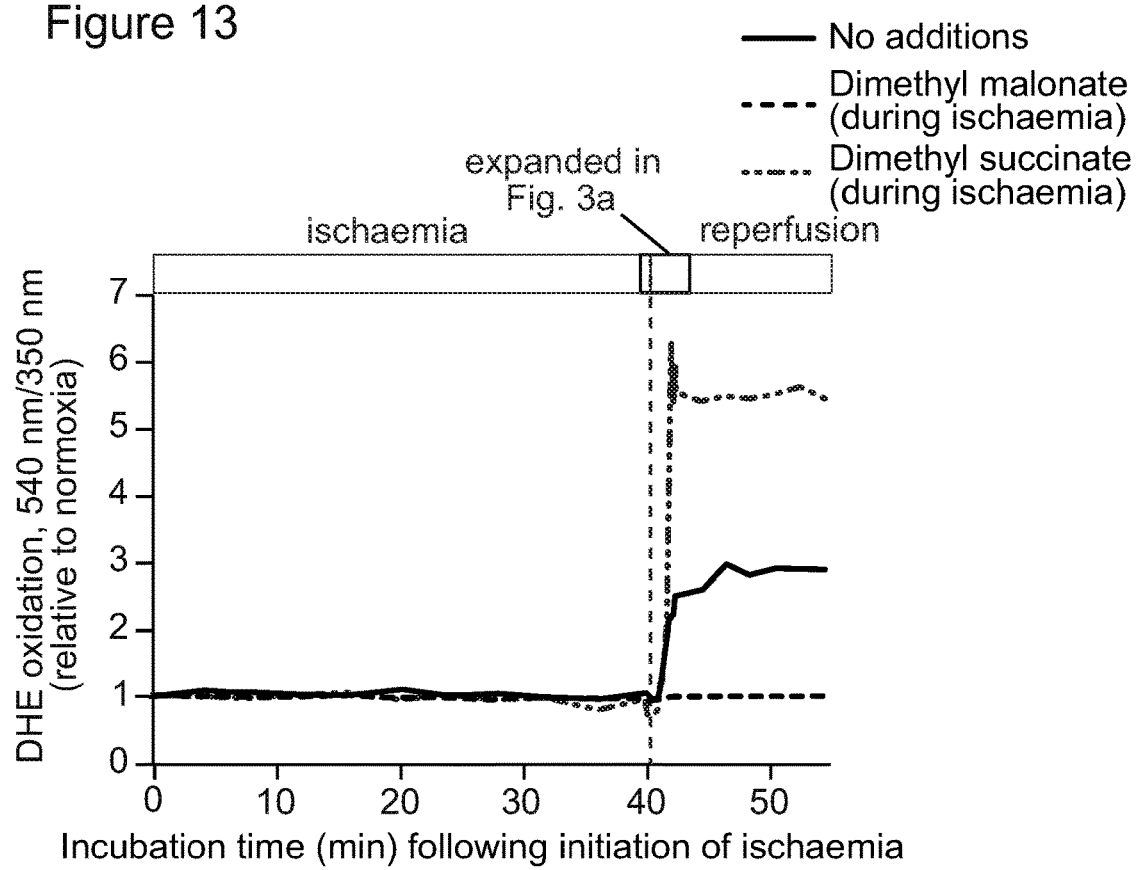
Figure 14:
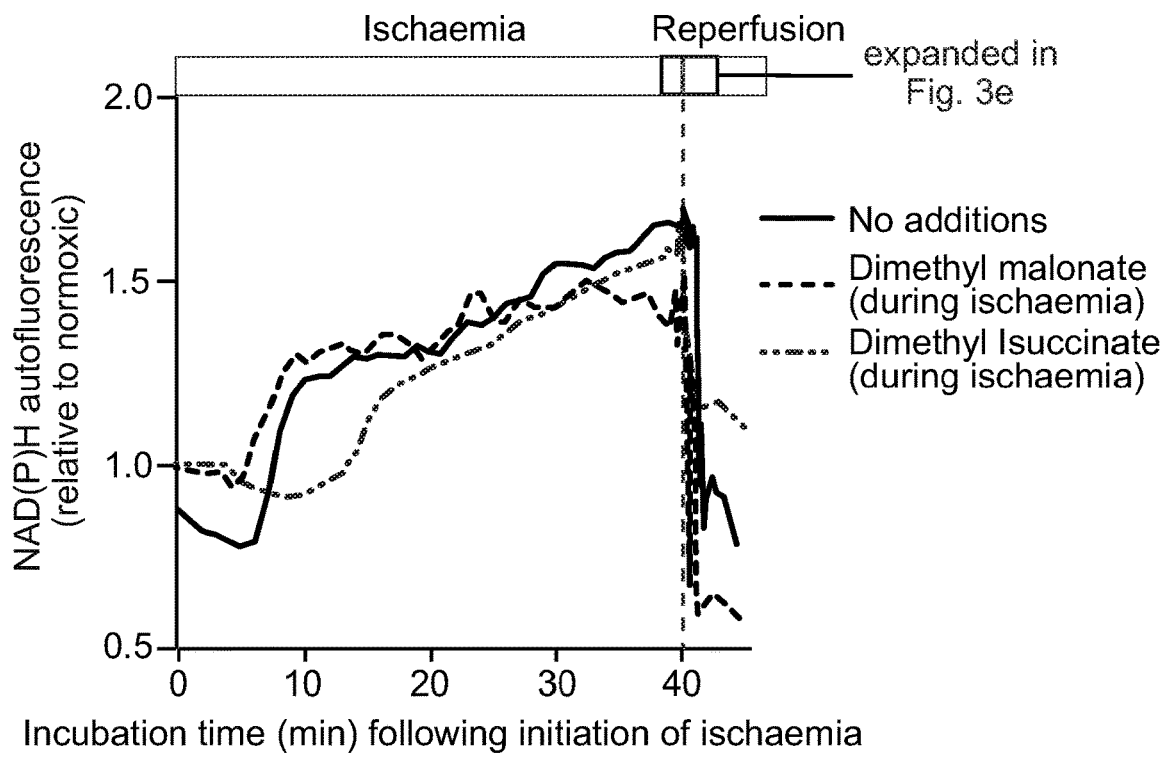
FIG. 14: Tracking NADH reduction state in primary cardiomyocytes during in situ IR. Primary rat cardiomyocytes were subjected to 40 min ischaemia and reoxygenation and NADH reduction state was tracked throughout the experiment by measurement of NAD(P)H autofluorescence. Ischaemic buffer contained either no additions, 4 mM dimethyl malonate, or 4 mM dimethyl succinate. Representative traces of each condition are shown. The highlighted window indicates the period of the experiment expanded in detail in FIG. 3c.
Figure 15:
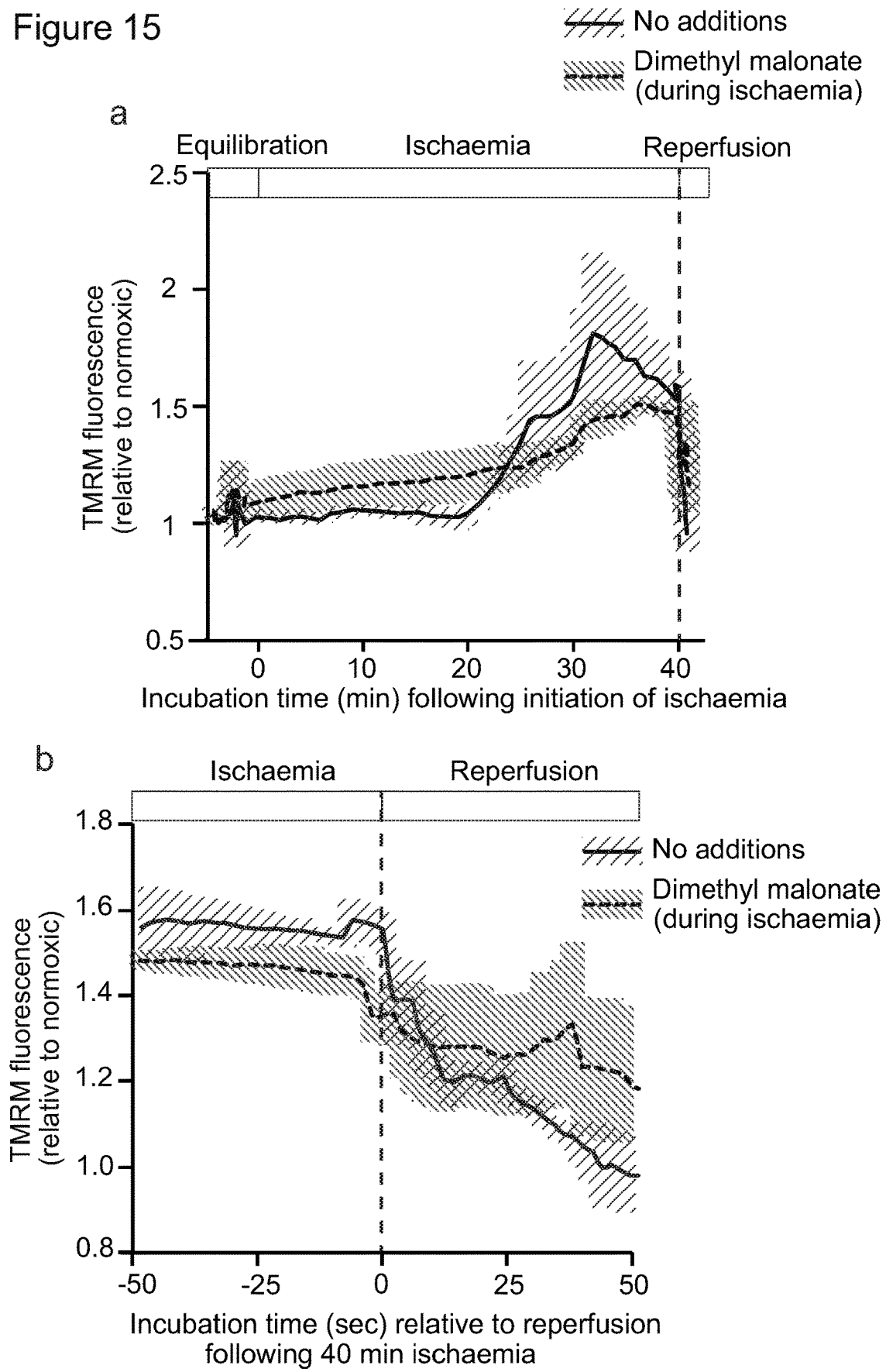
FIG. 15: Tracking mitochondrial membrane potential in primary cardiomyocytes during in situ IR. Primary rat cardiomyocytes were subjected to 40 min ischaemia and reoxygenation and mitochondrial membrane potential was tracked throughout the experiment by measurement of tetramethylrhoadmine (TMRM) fluorescence. Ischaemic buffer contained either no additions or 4 mM dimethyl malonate. Average traces from at least three replicate experiments are shown. (a) TMRM signal throughout the entire experiment.

To investigate the potential mechanisms underlying succinate-driven mitochondrial ROS production the inventors modelled how ischaemic cardiac metabolism alters upon reperfusion (FIG. 12). This analysis suggested that SDH would oxidise the accumulated succinate and thereby drive reverse electron transport (RET) through mitochondrial complex I[23-26]. Intriguingly, succinate drives extensive superoxide formation from complex I by RET in vitro, making it a compelling potential source of mitochondrial ROS during IR[26]. However, the role of complex I RET in IR injury has never been investigated. To test whether the succinate accumulated during ischaemia could drive complex I RET upon reperfusion, the inventors tracked mitochondrial ROS with the fluorescent probe dihydroethidine (DHE) and mitochondrial membrane potential from the potential-sensitive fluorescence of tetramethylrhodamine (TMRM), in a cardiomyocyte model of IR injury[27]. The rate of oxidation of DHE remained stable during ischaemia but rose rapidly upon reperfusion, consistent with increased superoxide production (FIGS. 3a and 13)[27]. Inhibition of SDH-mediated ischaemic succinate accumulation with dimethyl malonate reduced DHE oxidation upon reperfusion (FIG. 3a), whereas increasing succinate further during ischaemia with dimethyl succinate amplified reperfusion DHE oxidation, indicating that succinate levels controlled the extent of reperfusion ROS (FIG. 3b). Importantly, selective blocking of complex I RET with MitoSNO[8] abolished dimethyl succinate-driven DHE oxidation upon reperfusion (FIG. 3b), indicating that ischaemic succinate levels drove superoxide production through complex I RET. Succinate-dependent RET was further supported by the observation that NAD(P)H oxidation at reperfusion was suppressed by increasing succinate levels with dimethyl succinate (FIGS. 3c and 14). Tracking the mitochondrial membrane potential revealed that inhibition of ischaemic succinate accumulation diminished the rate of mitochondrial polarisation upon reperfusion (FIGS. 3d,e and 15), consistent with succinate-dependent enhanced complex I RET. Finally, elevating succinate in C2C12 mouse myoblast cells with dimethyl succinate while hyperpolarising mitochondria with oligomycin increased MitoSOX oxidation independently of IR (FIG. 3f), suggesting that combining high succinate levels with a large protonmotive force is sufficient to drive complex I ROS production by RET.

The inventors' findings may be explained by the following model (FIG. 4a): during ischaemia fumarate production increases, through activation of the MAS and PNC, and is then reduced to succinate by SDH reversal. Upon reperfusion, the accumulated succinate is rapidly oxidised, thereby sustaining a large protonmotive force and driving RET at complex I to produce the mitochondrial ROS that initiate IR injury[26]. This model provides a unifying framework for many hitherto unconnected aspects of IR injury, such as the requirement for priming during ischaemia to induce ROS upon reperfusion, protection against IR injury by the inhibition of complexes I[8] and II[28], and by mild uncoupling[29].

Figure 4:
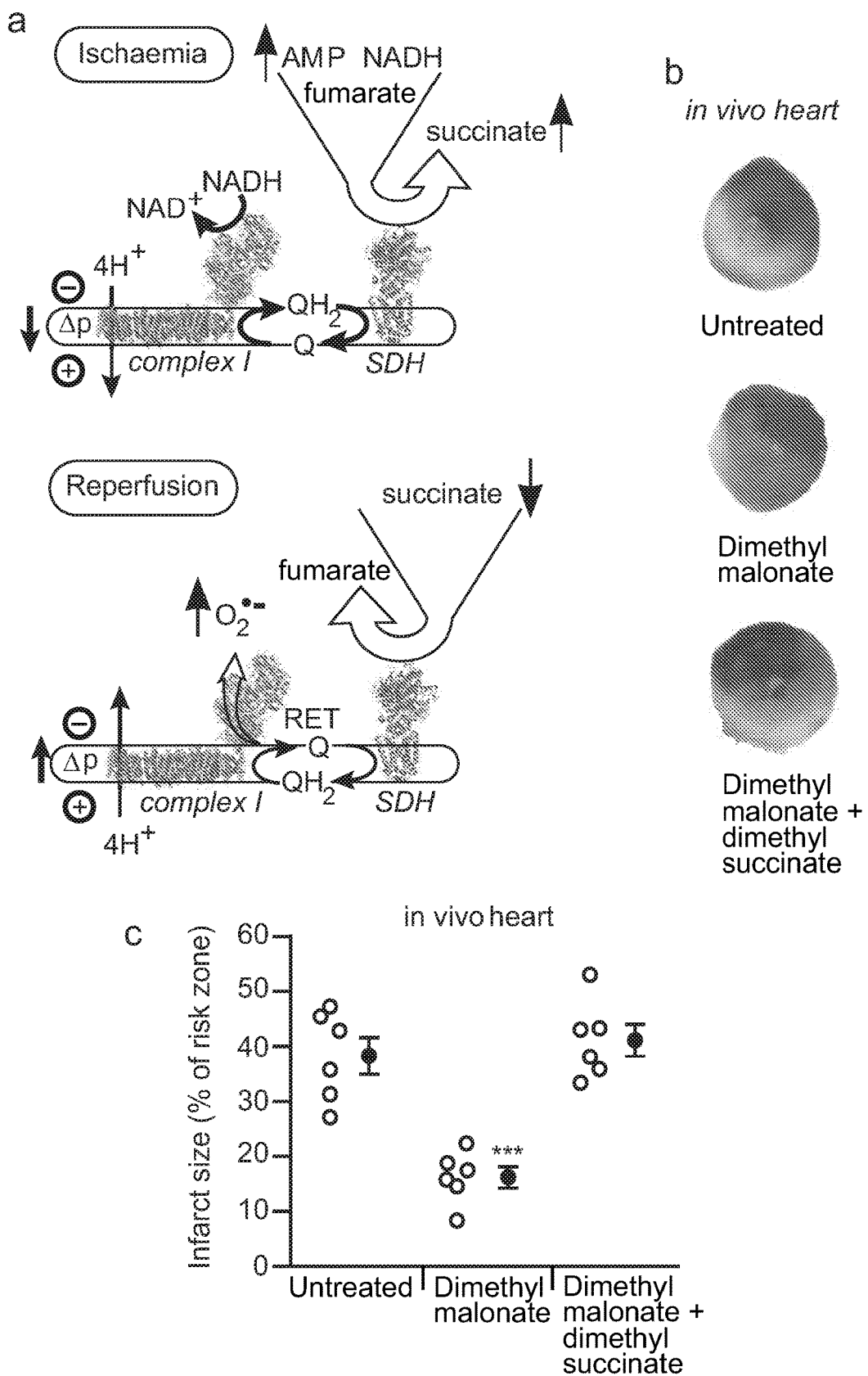
FIG. 4: NADH and AMP sensing pathways drive ischaemic succinate accumulation to control reperfusion pathologies in vivo through mitochondrial ROS production. (a) Model of succinate accumulation during ischaemia and superoxide formation by reverse electron transport (RET) during reperfusion.
Figure 4:
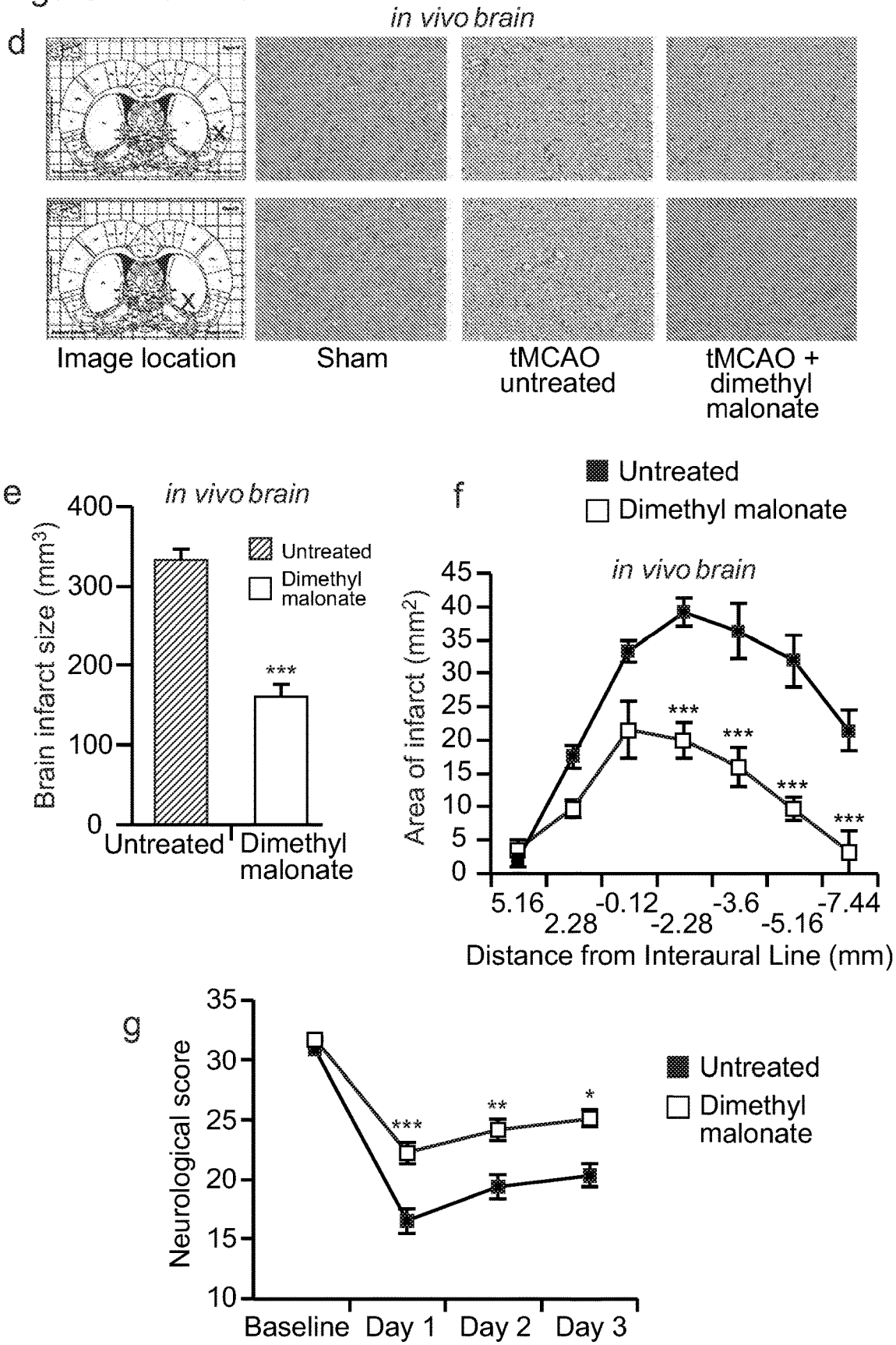

Intriguingly, the inventors' model also generates an unexpected, but testable, prediction. Manipulation of the pathways that increase succinate during ischaemia and oxidise it upon reperfusion should determine the extent of IR injury. Since the reversible inhibition of SDH blocks both succinate accumulation during ischaemia (FIG. 2b) and its oxidation upon reperfusion, it should protect against IR injury in vivo. Intravenous (i.v.) infusion of dimethyl malonate, a precursor of the SDH inhibitor malonate, during an in vivo model of cardiac IR injury was protective (FIGS. 4b,c). Importantly, this cardioprotection was suppressed by adding back dimethyl succinate (FIGS. 4b,c), indicating that protection resulted solely from blunting succinate accumulation. Finally, i.v. infusion of dimethyl malonate during rat brain transient middle cerebral artery occlusion (tMCAO), an in vivo model of brain IR injury during stroke, was protective, reducing the pyknotic nuclear morphology and vacuolation of the neuropil (FIG. 4d), decreasing the volume of infarcted brain tissue caused by IR injury (FIGS. 4e,f) and preventing the decline in neurological function associated with stroke (FIG. 4g and Table 2).

TABLE 2

Extended summary of neurological scores of rats subjected to tMCAO IR in vivo ± dimethyl malonate infusion.

| MCAO Control | Baseline | Day 1 | Day 2 | Day 3 |
| --- | --- | --- | --- | --- |
| Median Neurological Score | 31 | 16 | 19 | 20 |
| Average Neurological Score | 30.67 | 16.33 | 19.00 | 20.33 |
| Alpha | 0.05 | 0.05 | 0.05 | 0.05 |
| n | 6.00 | 6.00 | 6.00 | 6.00 |
| Standard Deviation | 0.82 | 2.25 | 2.37 | 2.34 |
| Confidence Interval | 0.29 | 1.10 | 1.06 | 1.02 |
| St Error | 0.33 | 0.92 | 0.97 | 0.95 |
| MCAO + Dimethyl malonate | Baseline | Day 1 | Day 2 | Day 3 |
| Median Neurological Score | 32.00 | 22.00 | 24.00 | 25.00 |
| Average Neurological Score | 31.67 | 22.67 | 24.00 | 24.33 |
| Alpha | 0.05 | 0.05 | 0.05 | 0.05 |
| n | 3.00 | 3.00 | 3.00 | 3.00 |
| Standard Deviation | 0.58 | 2.08 | 2.00 | 1.15 |
| Confidence Interval | 0.20 | 0.87 | 0.80 | 0.45 |
| St Error | 0.33 | 1.20 | 1.15 | 0.67 |

Extended data summary of median neurological scores in the three days following tMCAO IR ± dimethyl malonate described in FIG. 4g.

These findings validate the inventors' model of succinate-driven IR injury, demonstrating that succinate accumulation underlies IR injury in the heart and brain and validate the therapeutic approach of decreasing succinate accumulation and oxidation to treat IR injury.

The inventors have demonstrated that accumulation of succinate, via fumarate production and reversal of SDH, is a universal metabolic signature of ischaemia in vivo. In turn, succinate is a primary driver of the mitochondrial ROS production upon reperfusion that underlies IR injury in a range of tissues. Ischaemic accumulation of succinate may be of further relevance via its role in inflammatory and hypoxic signalling[10]. Thus succinate could contribute to both the acute pathogenesis of IR injury by mitochondrial ROS, and then upon secretion also trigger inflammation and neovascularisation[30]. Besides elucidating the metabolic responses that underlie IR injury, the inventors' have demonstrated that preventing succinate accumulation during ischaemia is protective against IR injury in vivo, thus, providing novel therapeutic targets for IR injury in pathologies such as heart attack and stroke.

Methods Summary

The following murine models of warm ischaemia and/or IR injury were used: global ischaemia of ex vivo perfused mouse heart; in vivo mouse left descending coronary artery (LAD) ligation; in vivo rat brain transient middle cerebral artery occlusion (tMCAO); in vivo mouse kidney ischaemia by monolateral occlusion of the renal hilum; in vivo global ischaemia of the liver following cervical dislocation. The modelling of metabolic pathways in the ischaemic myocardium was done as described previously[11]. The cell models of IR injury used were adult isolated primary rat cardiomyocytes and the mouse C2C12 myoblast cell line. Fluorescence within cardiomyocytes was assessed by laser scanning confocal microscopy. DHE fluorescence was used to measure ROS production, TMRM fluorescence in de-quench mode was used for mitochondrial membrane potential and NAD(P)H autofluorescence was used to assess the reduction potential of the NAD(P)H pools[8]. To assess metabolic pathways in the ex vivo perfused mouse heart $^{13}$C-labelled glucose, glutamine or aspartate were infused into the isolated heart and the $^{13}$C isotopologues of CAC metabolites were then quantified by LC-MS. The effects of metabolic inhibitors on ischaemic metabolite accumulation and the distribution of $^{13}$C-labels were assessed by i.v. infusion of metabolic inhibitors followed by LC-MS analysis of tissue metabolites. The redox state of the cardiac CoQ pool was assessed by LC. The amelioration of in vivo IR injury by metabolic inhibitors was assessed by i.v. administration of the inhibitors followed by measurement of the infarct size in the heart by triphenyltetrazolium chloride staining and in the brain by determining neurological function and infarct size by histology.

EXAMPLES

Methods

In Vivo Mouse Myocardial Experiments.
The mice used were C57BL/6J.
In Vivo Mouse Myocardial Experiments.

For the in vivo heart IR model an open-chest, in situ heart model was used[31,32]. Male mice (8-10 weeks; Charles River Laboratories, UK) were anaesthetised with sodium pentobarbital (70 mg/kg intraperitoneally (i.p.)), intubated endotracheally and ventilated with 3 cm $H_2O$ positive-end expiratory pressure. Adequacy of anaesthesia was monitored using corneal and withdrawal reflexes. Ventilation frequency was kept at 110 breaths per minute with tidal volume between 125-150 μL. A thoracotomy was performed and the heart exposed by stripping the pericardium. A prominent branch of the left anterior descending coronary artery (LAD) was surrounded by a 7-0 Prolene suture that was then passed through a small plastic tube. Ischaemia was induced by tightening the tubing against the heart surface. To assess metabolites during IR in vivo, mice were divided into three groups: 30 min ischaemia, 30 min ischaemia plus 5 min reperfusion and 30 min sham-operation in which the suture was placed but the LAD was not occluded. At the end of each protocol tissue was removed from the at risk and peripheral areas of the heart, selected visually by comparing white versus red tissue, and snap-frozen in liquid nitrogen. Sham-operated tissue was removed from the presumed risk zone.

Infarct size was assessed after 30 min of ischaemia followed by 120 min reperfusion using 2% triphenyltetrazolium chloride staining and is expressed as a percentage of the risk zone[33]. Metabolic inhibitors (all from Sigma) in sterile saline were infused i.v. via a tail vein to min prior to and throughout ischaemia at the following doses: dimethyl malonate (4 mg/kg/min), AOA (50 μg/kg/min; Fluorochem) and AICAR 10 mg/kg/min). Dimethyl succinate (8 mg/kg/min) was infused in combination with dimethyl malonate. Control mice were infused with sterile saline. The total volume administered never exceeded 200 μL/mouse.

Ex Vivo Langendorff Heart Experiments for Metabolomic Analysis.

Mice were heparinised (200 U i.p.) and anaesthetised with sodium pentobarbital (100 mg/kg i.p.). The chest was then opened and the heart rapidly excised and arrested in cold Krebs-Henseleit (KH) buffer (0.5 mM EDTA, 118 mM NaCl, 4.7 mM KCl, 25 mM $NaHCO_3$, 11 mM glucose, 1.2 mM $MgSO_4$, 1.2 mM $KH_2PO_4$ and 2 mM $CaCl_2$) at pH 7.4. The aorta was then cannulated with a 22 G blunt needle and transferred to a perfusion apparatus. The heart was perfused with 37° C. KH buffer (95% $O_2$/5% $CO_2$) at a constant pressure of 80 mm Hg. After 20 min equilibration hearts were separated into four groups: 60 min normoxic perfusion; 30 min global ischaemia; 30 min global ischaemia plus 5 min reperfusion; and 30 min global ischaemia plus 30 mins reperfusion. Metabolic inhibitors were infused for to min prior to ischaemia through a side port above the aortic cannula at 1% of coronary flow. At the end of the experiments the hearts were snap-frozen in liquid nitrogen and stored at −80° C.

$^{13}$C Metabolite Labelling in Ex Vivo Langendorff Heart Experiments.

Mice were anaesthetised with sodium pentobarbital (~140 mg/kg). Hearts were rapidly excised, cannulated and perfused in the isovolumic Langendorff mode at 80 mm Hg perfusion pressure, at 37° C. with KH buffer continuously gassed with 95% $O_2$/5% $CO_2$ (pH 7.4)[34]. Cardiac function was assessed using a fluid-filled balloon inserted into the left ventricle (LV), and connected to a pressure transducer and a PowerLab™ system (ADinstruments, UK). Balloon volume was adjusted to an initial LV diastolic pressure of 4-9 mm Hg[34] and all hearts were paced at 550 bpm. Left ventricular developed pressure (LVDP) was calculated from the difference between systolic (SP) and diastolic pressures (DP). Functional parameters (SP, end diastolic pressure, heart rate, LVDP, coronary flow, perfusion pressure) were recorded continuously using LabChart™ software v.7 (ADinstruments, UK).

After 20 min equilibration with standard KH buffer, hearts were divided into the following groups: perfused with KH buffer containing 11 mM U-$^{13}$C Glucose followed by 30 min normoxic respiration (n=4/group); perfused for 10 min with KH buffer containing 11 mM U-$^{13}$C glucose and then subjected to 30 min global normothermic 10 ischaemia (n=4/group); perfusion of KH buffer containing 1 mM 5-$^{13}$C L-glutamine for 10 min followed by standard normoxic perfusion for 30 min with unlabeled KH buffer (n=4); 10 min perfusion with 1 mM $^{13}C_5$ L-glutamine, followed by 30 min global ischaemia (n=4); 10 min perfusion of 1 mM 1-$^{13}C$ L-aspartic acid, followed by normoxic perfusion for 30 min with unlabeled KH buffer; 10 min perfusion with 1 mM 1-$^{13}C$ L-aspartic acid, followed by 30 min global ischaemia. At the end hearts were snap frozen in liquid nitrogen and stored at −80° C.

In Vivo Rat Brain Ischaemia and Reperfusion.

Male spontaneously hypertensive stroke prone (SHRSP) rats from the colony maintained at the University of Glasgow (270-310 g) were anaesthetised with 5% isoflurane in oxygen and were intubated and ventilated throughout surgery (~2.5% isoflurane/oxygen). Body temperature was maintained at 37±0.5° C. Animals underwent pre-stroke burrhole surgery[35] before transient middle cerebral artery occlusion (tMCAO, 45 min). Briefly, a silicone-coated monofilament was advanced (Doccol Corporation, USA) was advanced through the common carotid artery to block the origin of the MCA[36]. Animals were maintained under anaesthesia during ischaemia. Immediately following removal of the filament, or after 5 mins of reperfusion, the brain was removed following cervical dislocation and infarct tissue separated from surrounding tissue on the ipsilateral side and snap frozen in liquid nitrogen for metabolomic analysis. Corresponding regions were taken from the contralateral side. A separate group was infused with dimethyl malonate (6 mg/kg/min) by i.v. infusion 10 min prior to and during tMCAO) or carrier, allowed to recover for 3 days, over which time they were scored for neurological function[37] as modified[38]. These rats were then sacrificed by transcardiac perfusion fixation and the infarct area was assessed across 7 coronal levels following hematoxylin and eosin staining[39].

In Vivo Mouse Renal Ischaemia and Reperfusion.

Under isofluorane general anaesthesia, mice underwent laparotomy and exposure of the renal hilum bilaterally. Vascular clips (8 mm, InterFocus Fine Science Tools, Cambridge, UK) were placed over one renal hila to induce unilateral renal ischaemia. At the end of 45 min ischaemia the clip was removed and reperfusion of the kidney noted as return of blush colour and visualisation of flow from the renal vein. Kidneys were taken at the end of ischaemia, or following 5 min reperfusion and snap-frozen in liquid nitrogen for metabolomic analysis.

In Vivo Mouse Liver Warm Ischaemia.

Mice were killed by cervical dislocation to ensure cessation of blood flow. Liver tissue was maintained in situ in the body cavity for 45 min at 37° C. through use of a thermostated heat pad followed by removal and snap-freezing on liquid nitrogen for subsequent metabolomic analysis.

Metabolomic Analyses.

Equal amounts wet weight murine tissue were lysed in 250 µL extraction solution (ES; 30% acetonitrile, 50% methanol and 20% water) per 10 mg tissue in Precellysis 24 vials, following the manufacturer's instructions. The suspension was immediately centrifuged (16,000 g, 15 min at 0° C.) and the supernatant used for LC-MS analysis. For the LC separation, column A was Sequant Zic-Hilic (150 mm×4.6 mm, internal diameter 3.5 µm) with a guard column (20 mm×2.1 mm 3.5 µm) from HiChrom, Reading, UK. Mobile phases. A: 0.1% formic acid (v/v) in water. B: 0.1% formic acid (v/v) in acetonitrile. Flow rate 300 µL/min. Gradient: 0-3 min 80% B, 25 min 20% B, 26 min 80% B, 36 min 80% B. Column B was sequant Zic-pHilic (150 mm×2.1 mm i.d. 3.5 µm) with guard column (20 mm×2.1 mm i.d. 3.5 Mm) from HiChrom, Reading, UK. Mobile phases. C: 20 mM ammonium carbonate plus 0.1% ammonium hydroxide in water. D: acetonitrile. Flow rate 100 µL/min. Gradient: 0 min 80% D, 28 min 20% D, 29 min 80% D, 45 min 80% D. The mass spectrometer (Thermo QExactive Orbitrap) was operated in full MS and polarity switching mode. Samples were randomised in order to avoid machine drifts. Spectra were analysed using both targeted and untargeted approaches. For the targeted approach spectra were analysed using XCalibur Qual Browser and XCalibur Quan Browser softwares (Thermo Scientific) by referencing to an internal library of compounds. For the untargeted approach spectra were processed with Sieve™ 2.0 software (Thermo Scientific) and spectral peaks were extracted. The arrays of spectra were then statistically analysed using the functions explore.data and univariate of the R package mum a[40].

In Situ Ischaemia and Reperfusion of Adult Rat Primary Cardiomyocytes.

Male Sprague-Dawley rats (300-370 g) were terminally anaesthetised via IP injections of 200 mg/kg sodium pentobarbitone and 330 U/kg heparin. Hearts were excised and retrograde perfused on a Langendorff-perfusion system with 13 mL/min oxygenated KH buffer at 37° C. Cells were isolated by collagenase digestion using standard methods[41]. Briefly, hearts were perfused for 5 min with KH buffer, then 5 min with $Ca^{2+}$-free KH buffer containing 100 µM EGTA, followed by 8 min with KH buffer containing 100 µM $CaCl_2$ and 0.5 mg/ml collagenase II (Worthington). The heart was removed from the cannula and ventricles quickly chopped and bathed in 20 mL of the same collagenase buffer for 15 min. Digested tissue was passed through a 100 µm cell filter, and cells were collected by gravity. The supernatant was removed and cells were washed with KH buffers containing first 0.5 mM $CaCl_2$, then 1 mM $CaCl_2$. Typical yields were $2 \times 10^6$ cells/heart with 90% viable, rod-shaped cells. The cells were resuspended in Medium 199 (supplemented with 5 mM creatine, 2 mM carnitine, 5 mM taurine, and 100 µg/mL penicillin/streptomycin) and plated onto coverslips coated with laminin (Sigma). After 1 h incubation at 37° C./5% $CO_2$, unattached cells were washed off, and fresh Medium 199 was added to each well for at least 4 h at 37° C./5% $CO_2$.

Cells were imaged within 36 hours of plating. Images using a Zeiss™ LSM 510 META confocal microscope with a Fluar 20×/0.75 NA UV objective, or a microscope equipped with an Orca™ ER cooled CCD camera (Hamamatsu), a monochrometer (Cairn Research) and emission filter wheel (Prior) with a Fluar 20×/0.75 NA objective. Cells attached to coverslips, which formed the base of custom built imaging chambers, were placed on a heated stage at 37° C. on the microscope with normoxic recording buffer (156 mM NaCl, 3 mM KCl, 2 mM $MgSO_4$, 1.25 mM $KaHPO_4$, 2 mM $CaCl_2$, 10 mM Hepes, 10 mM D-Glucose; pH 7.4). Simulated ischaemia was achieved by replacing the buffer with a pre-gassed, hypoxic recording buffer simulating ischaemia (as above but lacking glucose and containing 10 mM sodium lactate, 14.8 mM KCl; pH 6.4) and by covering the heated stage with a transparent, gas-impermeant lid, forming a small chamber into which argon was forced to maintain hypoxia. $pO_2$ was routinely measured as <2.0 mm Hg during simulated ischaemia. To simulate reperfusion, the lid was removed from the chamber, and the buffer replaced with normoxic recording buffer.

Mitochondrial membrane potential was measured using tetramethylrhodamine, methyl ester (TMRM, Life Technologies) in dequench mode. In this mode, mitochondrial depolarisation causes redistribution of a high concentration of quenched TMRM from mitochondria to cytosol, where the lower concentration results in dequenching and an increase in fluorescence[27]. Cells were loaded at room temperature with normoxic recording buffer containing 3 µM TMRM for 30 min. Prior to imaging, loading buffer was removed and replaced with normoxic recording buffer. TMRM fluorescence was excited at 543 nm and emission was collected using a LP 560 filter.

ROS production was estimated by oxidation of DHE. For this cells were loaded with 5 µM dihydroethidium (DHE, Invitrogen), which remained present throughout normoxic and ischaemic conditions. DHE was excited at 351 nm and the emitted signal was acquired with a BP 435-485 IR filter. Oxidised DHE was excited at 543 nm and emission was collected with a LP 560 filter. NADH autofluorescence was excited at 351 nm and the emitted signal was collected using a BP 435-485IR filter. All measured cell parameters were analysed with Fiji image processing software.

Assessment of Succinate-Dependent Mitochondrial Superoxide Production in Myoblasts.

C2C12 myoblasts were seeded in 35 mm glass bottom culture dishes (MatTek) and incubated for 24 h in low glucose (1 g/L) DMEM. 2 h prior to imaging DMEM was removed, and replaced with imaging buffer (132 mM NaCl; to mM HEPES; 4.2 mM KCl; 1 mM $MgCl_2$ 1 mM $CaCl_2$ adjusted to pH 7.4 with Tris base and supplemented with 2-deoxyglucose (25 µM), and sodium pyruvate (10 mg/L or 4 µM oligomycin as indicated). Myoblasts were pre-incubated with 2 µM MitoSOX for 15 min prior to imaging. MitoSOX fluorescence was monitored using a Nikon Eclipse Ti confocal microscope at 37° C. on a temperature controlled stage for 30 min. MitoSOX was excited at 510 nm and the emitted signal collected with a LP 560 filter following the indicated additions.

In Silico Analysis of Metabolic Flux During Ischaemia and Reperfusion.

Simulations were performed using an expanded version of the myocardial mitochondrial metabolic model iAS253[11]. The model was expanded to include additional mitochondrial reactions by using the latest version of MitoMiner, a mitochondrial proteomics database[42]. MitoMiner was used to identify new mitochondrial reactions for inclusion by cross-referencing these data with information from BRENDA[43], HumanCyc[44] and relevant literature to confirm that the new reactions are present in human, expressed in heart tissue and localised to the mitochondrial matrix. In addition, cytosolic reactions were included that could contribute to energy production, such as amino acid degradation and conversion reactions as well as the purine nucleotide cycle. Protonation states of metabolites in the model were calculated by using the Marvin suite of computational chemistry software (ChemAxon Ltd, Budapest, Hungary). Reactions were then charge-balanced according to the protonation state of the major microspecies found at pH 8.05 for the mitochondrial matrix[45] and pH 7.30 for the cytosol. In addition directionality constraints were imposed based upon general rules of irreversibility, thermodynamics and information from public resources such as BRENDA and HumanCyc and capacity constraints were taken from the literature[11]. The final model contained 227 mitochondrial matrix reactions, 76 cytosolic reactions, 91 transport steps between the two compartments and 84 boundary conditions representing inputs and outputs into the system. The expanded model is a manually curated and highly refined model of the mitochondrion, and as with iAS253, no metabolite dead ends were present and all reactions were capable of having flux.

To represent ischaemia, the maximum uptake of oxygen was reduced to 5% of its level under normal conditions (0.99 vs. 19.8 µmol/min/gram dry weight). To represent reperfusion, the oxygen level was restored to its normal level and the availability of succinate, lactate, pyruvate and NADH was increased to various levels so to reflect the ischemic accumulation of these metabolites. The flux capacity of ATP synthase was reduced by up to 50% to represent the delay in generating ADP from AMP required for ATP synthase to function and also to model hyper-polarisation of the mitochondrial membrane, in effect by constraining the efficiency of the other proton pumping complexes of the electron transport chain.

Metabolism of the mitochondrial network was simulated using flux balance analysis, a technique that has been described in detail elsewhere[46]. The objective function used to optimise the reaction fluxes was maximum ATP production. All the FBA simulations were carried out using MATLAB™ R2012b (Math Works, Inc, Natick, Mass.) with the COBRA Toolbox[47], and the linear programming solver GLPK (http://www.gnu.org/software/glpk).

REFERENCES

1. Murphy, E. & Steenbergen, C. Mechanisms underlying acute protection from cardiac ischemia-reperfusion injury. *Physiol. Rev.* 88, 581-609, (2007).
2. Yellon, D. M. & Hausenloy, D. J. Myocardial reperfusion injury. *N. Engl. J. Med.* 357, 1121-1135, (2007).
3. Burwell, L. S., Nadtochiy, S. M. & Brookes, P. S. Cardioprotection by metabolic shut-down and gradual wake-up. *J. Mol. Cell. Cardiol.* 46, 804-810, (2009).
4. Eltzschig, H. K. & Eckle, T. Ischemia and reperfusion—from mechanism to translation. *Nat. Med.* 17, 1391-1401, (2011).
5. Timmers, L et al. The innate immune response in reperfused myocardium. *Cardiovasc. Res.* 94, 276-283, (2012).
6. Harmsen, E., de Jong, J. W. & Serruys, P. W. Hypoxanthine production by ischemic heart demonstrated by high pressure liquid chromatography of blood purine nucleosides and oxypurines. *Clin. Chim. Acta* 115, 73-84 (1981).
7. Pacher, P., Nivorozhkin, A. & Szabo, C. Therapeutic effects of xanthine oxidase inhibitors: renaissance half a century after the discovery of allopurinol. *Pharmacol. Revs.* 58, 87-114, (2006).
8. Chouchani, E. T. et al. Cardioprotection by S-nitrosation of a cysteine switch on mitochondrial complex I. *Nat. Med.* 19, 753-759, (2013).
9. Zweier, J. L, Flaherty, J. T. & Weisfeldt, M. L Direct measurement of free radical generation following reperfusion of ischemic myocardium. *Proc. Natl. Acad. Sci. USA* 84, 1404-1407 (1987).
10. Tannahill, G. M. et al. Succinate is an inflammatory signal that induces IL-tbeta through HIF-1alpha. *Nature* 496, 238-242, (2013).
11. Smith, A. C. & Robinson, A. J. A metabolic model of the mitochondrion and its use in modelling diseases of the tricarboxylic acid cycle. *BMC Syst. Biol.* 5, 102, (2011).
12. Pisarenko, O. I. et al. On the mechanism of enhanced ATP formation in hypoxic myocardium caused by glutamic acid. *Basic Res. Cardiol.* 80, 126-134 (1985).
13. Taegtmeyer, H. Metabolic responses to cardiac hypoxia. Increased production of succinate by rabbit papillary muscles. *Circ. Res.* 43, 808-815 (1978).

14. Hochachka, P. W. & Storey, K. B. Metabolic consequences of diving in animals and man. *Science* 187, 613-621 (1975).
15. Easlon, E., Tsang, F., Skinner, C., Wang, C. & Lin, S. J. The malate-aspartate NADH shuttle components are novel metabolic longevity regulators required for calorie restriction-mediated life span extension in yeast. *Genes Dev.* 22, 931-944, (2008).
16. Barron, J. T., Cu, L & Parrillo, J. E. Malate-aspartate shuttle, cytoplasmic NADH redox potential, and energetics in vascular smooth muscle. *J. Mol. Cell. Cardiol.* 30, 1571-1579, (1998).
17. Van den Berghe, G., Vincent, M. F. & Jaeken, J. Inborn errors of the purine nucleotide cycle: adenylosuccinase deficiency. *J. Inherit. Metab. Dis.* 20, 193-202 (1997).
18. Sridharan, V. et al. $O_2$-sensing signal cascade: clamping of $O_2$ respiration, reduced ATP utilization, and inducible fumarate respiration. *Amer. J. Physiol.* 295, C29-37, (2008).
19. Dervartanian, D. V. & Veeger, C. Studies on succinate dehydrogenase. I. spectral properties of the purified enzyme and formation of enzyme-competitive inhibitor complexes. *Biochim. Biophvs. Acta* 92, 233-247 (1964).
20. Gutman, M. Modulation of mitochondrial succinate dehydrogenase activity, mechanism and function. *Mol. Cell. Biochem.* 20, 41-60 (1978).
21. Bunger, R., Glanert, S., Sommer, O. & Gerlach, E. Inhibition by (aminooxy)acetate of the malate-aspartate cycle in the isolated working guinea pig heart. *Hoppe Seyvlers Z. Physiol. Chem.* 361, 907-914 (1980).
22. Swain, J. L, Hines, J. J., Sabina, R. L, Harbury, O. L. & Holmes, E. W. Disruption of the purine nucleotide cycle by inhibition of adenylosuccinate lyase produces skeletal muscle dysfunction. *J. Clin. Invest.* 74, 1422-1427, (1984).
23. Hirst, J., King, M. S. & Pryde, K. R. The production of reactive oxygen species by complex I. *Biochem. Soc. Trans.* 36, 976-980 (2008).
24. Kussmaul, L & Hirst, J. The mechanism of superoxide production by NADH:ubiquinone oxidoreductase (complex I) from bovine heart mitochondria. *Proc. Natl. Acad. Sci. USA* 103, 7607-7612 (2006).
25. Pryde, K. R. & Hirst, J. Superoxide is produced by the reduced flavin in mitochondrial complex I: a single, unified mechanism that applies during both forward and reverse electron transfer. *J. Biol. Chem.* 286, 18056-18065, (2011).
26. Murphy, M. P. How mitochondria produce reactive oxygen species. *Biochem. J.* 417, 1-13, (2009).
27. Davidson, S. M., Yellon, D. & Duchen, M. R. Assessing mitochondrial potential, calcium, and redox state in isolated mammalian cells using confocal microscopy. *Methods Mol. Biol.* 372, 421-430, (2007).
28. Wojtovich, A. P., Smith, C. O., Haynes, C. M., Nehrke, K. W. & Brookes, P. S. Physiological consequences of complex II inhibition for aging, disease, and the mKATP channel. *Biochim. Biophys. Acta* 1827, 598-611, (2013).
29. Brennan, J. P. et al. Mitochondrial uncoupling, with low concentration FCCP, induces ROS-dependent cardioprotection independent of KATP channel activation. *Cardiovas. Res.* 72, 313-321, (2006).
30. Hamel, D. et al. G-Protein-coupled receptor 91 and succinate are key contributors in neonatal postcerebral hypoxia-ischemia recovery. *Arterioscler. Throm b. Vasc. Biol.* 34, 285-293, (2014).
31. Schmidt, K. et al. Cardioprotective effects of mineralocorticoid receptor antagonists at reperfusion. *Eur. Heart J.* 31, 1655-1662, (2010).
32. Methner, C. et al. Protection through postconditioning or a mitochondria-targeted S-nitrosothiol is unaffected by cardiomyocyte-selective ablation of protein kinase G. *Basic Res. Cardiol.* 108, 337, (2013).
33. Nadtochiy, S. M., Redman, E., Rahman, I. & Brookes, P. S. Lysine deacetylation in ischaemic preconditioning: the role of SIRT1. *Cardiovasc. Res.* 89, 643-649, (2011).
34. Ashrafian, H. et al. Fumarate is cardioprotective via activation of the Nrf2 antioxidant pathway. *Cell Metab.* 15, 361-371, (2012).
35. Ord, E. N. J., Shirley, R., van Kralingen, J. C., Graves, A., McClure, J. D., Wilkinson, M., McCabe, C., Macrae, I. M. & Work, LM. Positive impact of pre-stroke surgery on survival following transient focal ischemia in hypertensive rats. *J. Neurosci. Methods* 211, 305-308, (2012).
36. Koizumi, J., Yoshida, Y., Nakazawa, T. & Ooneda, G. Experimental studies of ischemic brain edema: a new experimental model of cerebral embolism in rats in which recirculation can be introduced in the ischemic area. *Jpn. J. Stroke* 8, 1-8 (1986).
37. Hunter, A. J., et al., Functional assessments in mice and rats after focal stroke. *Neuropharmacology.* 39, 806-816, (2000).
38. Ord, E. N. J. et al., Combined antiapoptotic and antioxidant approach to acute neuroprotection for stroke in hypertensive rats. *J. Cereb. Blood Flow Metab.* 33, 1215-1224, (2013).
39. Osborne, K. A. et al. Quantitative assessment of early brain damage in a rat model of focal cerebral ischaemia. *J. Neurol. Neurosurg. Psychiatry* 50, 402-410 (1987).
40. Gaude, E. et al. muma, An R Package for metabolomics univariate and multivariate statistical analysis. *Current Metabol.* 1, 180-189 (2013).
41. Davidson, S. M. & Duchen, M. R. Effects of NO on mitochondrial function in cardiomyocytes: Pathophysiological relevance. *Cardiovasc. Res.* 71, 10-21, (2006).
42. Smith, A. C., Blackshaw, J. A. & Robinson, A. J. MitoMiner: a data warehouse for mitochondrial proteomics data. *Nucleic Acids Res.* 40, (2012).
43. Chang, A., Scheer, M., Grote, A., Schomburg, 1. & Schomburg, D. BRENDA, AMENDA and FRENDA the enzyme information system: new content and tools in 2009. *Nucleic Acids Res.* 37, D588-592, (2009).
44. Romero, P. et al. Computational prediction of human metabolic pathways from the complete human genome. *Genome Biol.* 6, $R^2$, (2005).
45. Abad, M. F., Di Benedetto, G., Magalhaes, P. J., Filippin, L & Pozzan, T. Mitochondrial pH monitored by a new engineered green fluorescent protein mutant. *J. Biol. Chem.* 279, 11521-11529, (2004).
46. Orth, J. D., Thiele, 1. & Palsson, B. O. What is flux balance analysis? Nat. *Biotechnol.* 28, 245-248, (2010).
47. Becker, S. A. et al. Quantitative prediction of cellular metabolism with constraint-based models: the COBRA Toolbox. *Nat. Prot.* 2, 727-738, (2007).

All publications mentioned in the above specification are herein incorporated by reference. Although illustrative embodiments of the invention have been disclosed in detail herein, with reference to the accompanying drawings, it is understood that the invention is not limited to the precise embodiment and that various changes and modifications can be effected therein by one skilled in the art without departing from the scope of the invention as defined by the appended claims and their equivalents.

What is claimed:

1. A method for treating a reperfusion injury in the heart, intestine, kidney, lung, pancreas and skin of a subject, the method comprising administering to the subject a therapeutically effective amount of a cell-permeable and reversible succinate dehydrogenase inhibitor that is selected from $R^1O_2C—CH_2—CO_2R^4$, $R^1O_2C—CH(OH)—CH_2—CO_2R^4$, or $R^1O_2C—CH_2—C(O)—CO_2R^4$; wherein:

$R^1$ is selected from straight chain or branched chain $C_{1-12}$ alkyl; and $R^4$ is selected from straight chain or branched chain $C_{1-12}$ alkyl.

2. The method of claim 1, wherein the inhibitor is selected from $R^1O_2C—CH_2—CO_2R^4$, wherein $R^1$ and $R^4$ are independently selected from methyl, ethyl, propyl and butyl.

3. The method of claim 1, wherein the inhibitor is $CH_3O_2C—CH_2—CO_2CH_3$.

4. The method of claim 1, wherein the reperfusion injury is a result of disorder selected from the group consisting of: abdominal aortic aneurysm, atherosclerosis, artery disease, burns, cancer, cardiac arrest, cerebrovascular disease, cerebral edema secondary to stroke, chronic obstructive pulmonary disease, congestive heart disease, constriction after percutaneous transluminal coronary angioplasty, coronary disease, diabetes, hypertension, mechanical trauma resulting from crush injury or surgery, migraine, myocardial infarction, peripheral vascular disease, pulmonary vascular disease, reperfusion after cardiac surgery, reperfusion after stroke, retinal vascular disease, stroke and surgical tissue reperfusion injury.

5. The method of claim 1, wherein the reperfusion injury is an ischaemia-reperfusion injury.

6. The method of claim 1, wherein the reperfusion injury is the result of an elective surgery.

7. The method of claim 1, wherein the reperfusion injury is the result of an organ transplantation.

8. The method of claim 1, further comprising administering a treatment used to or intended to remove a blockage in blood flow.

9. The method of claim 8, wherein the treatment is selected from the group consisting of: blood thinning agents, lysis agents, MitoSNO and stents.

10. The method of claim 1, wherein the inhibitor inhibits the accumulation of succinate.

11. The method of claim 1, wherein the cell-permeable and reversible succinate dehydrogenase inhibitor is administered before the reperfusion injury.

12. The method of claim 6, wherein the cell-permeable and reversible succinate dehydrogenase inhibitor is administered before the elective surgery.

13. The method of claim 1, wherein the subject is at risk for the reperfusion injury.

* * * * *